US009545294B2

(12) United States Patent
Liebman

(10) Patent No.: US 9,545,294 B2
(45) Date of Patent: Jan. 17, 2017

(54) COMPONENTS, SYSTEM AND METHOD FOR MAKING DENTURES IN A SINGLE VISIT

(71) Applicant: Arnold I. Liebman, Brooklyn, NY (US)

(72) Inventor: Arnold I. Liebman, Brooklyn, NY (US)

( * ) Notice: Subject to any disclaimer, the term of this patent is extended or adjusted under 35 U.S.C. 154(b) by 757 days.

(21) Appl. No.: 13/905,642

(22) Filed: May 30, 2013

(65) Prior Publication Data

US 2014/0356806 A1 Dec. 4, 2014

(51) Int. Cl.
*A61C 9/00* (2006.01)
*A61C 13/34* (2006.01)
*A61C 11/08* (2006.01)

(52) U.S. Cl.
CPC ............... *A61C 13/34* (2013.01); *A61C 9/002* (2013.01); *A61C 9/0006* (2013.01); *A61C 11/088* (2013.01)

(58) Field of Classification Search
CPC ....... A61C 13/34; A61C 9/0006; A61C 9/002; A61C 11/088
USPC .......................................................... 433/37
See application file for complete search history.

(56) References Cited

U.S. PATENT DOCUMENTS 4,265,619 A * 5/1981 Lucki .................... A61C 9/002
433/213
8,070,489 B2 * 12/2011 Massad .................. A61C 19/05
433/71
2006/0216667 A1 * 9/2006 Jung ...................... A61C 9/002
433/60
2010/0075273 A1 * 3/2010 Karlsson .............. A61C 9/0006
433/44

OTHER PUBLICATIONS

How it Works, Denta.com, available at: http://www.dentca.com/how.asp.
PALA Denture Equipment, Heraeus Kulzer North America, available at: http://heraeus-dental-us.com/en/ourproducts/laboratory_2/equipment/equipment_1.aspx.
Aldo Leopardi, Complete Denture Therapy: Removable prosthodontics has a significant and rewarding role in modern clinical practice, vol. 7, Issue 5 (May 2011), available at: http://www.dentalaegis.com/id/2011/05/removable-prosthodontics-significant-and-rewarding-role-in-modern-clinical-practice.

* cited by examiner

*Primary Examiner* — Cris L Rodriguez
*Assistant Examiner* — Mirayda A Aponte
(74) *Attorney, Agent, or Firm* — Andrew S. Langsam; Pryor Cashman LLP

(57) ABSTRACT

Creating a denture by using the patient's mouth as an intra-oral articulator by use of an upper and/or lower dental impression tray for creating the impression of the edentulous mouth, the trays having platforms or support surfaces which magnetically hold a main frame therebetween. The orientation of the main frame is adjustable and lockable with respect to the lower tray all while within the mouth. Once the main frame is located and locked in place, artificial teeth formed with holding wax and a rearwardly extending fork are slid into a slot of the main frame and also locked. The wax holding the artificial teeth is then melted to integrate the teeth with formed respective upper and lower custom trays.

7 Claims, 23 Drawing Sheets

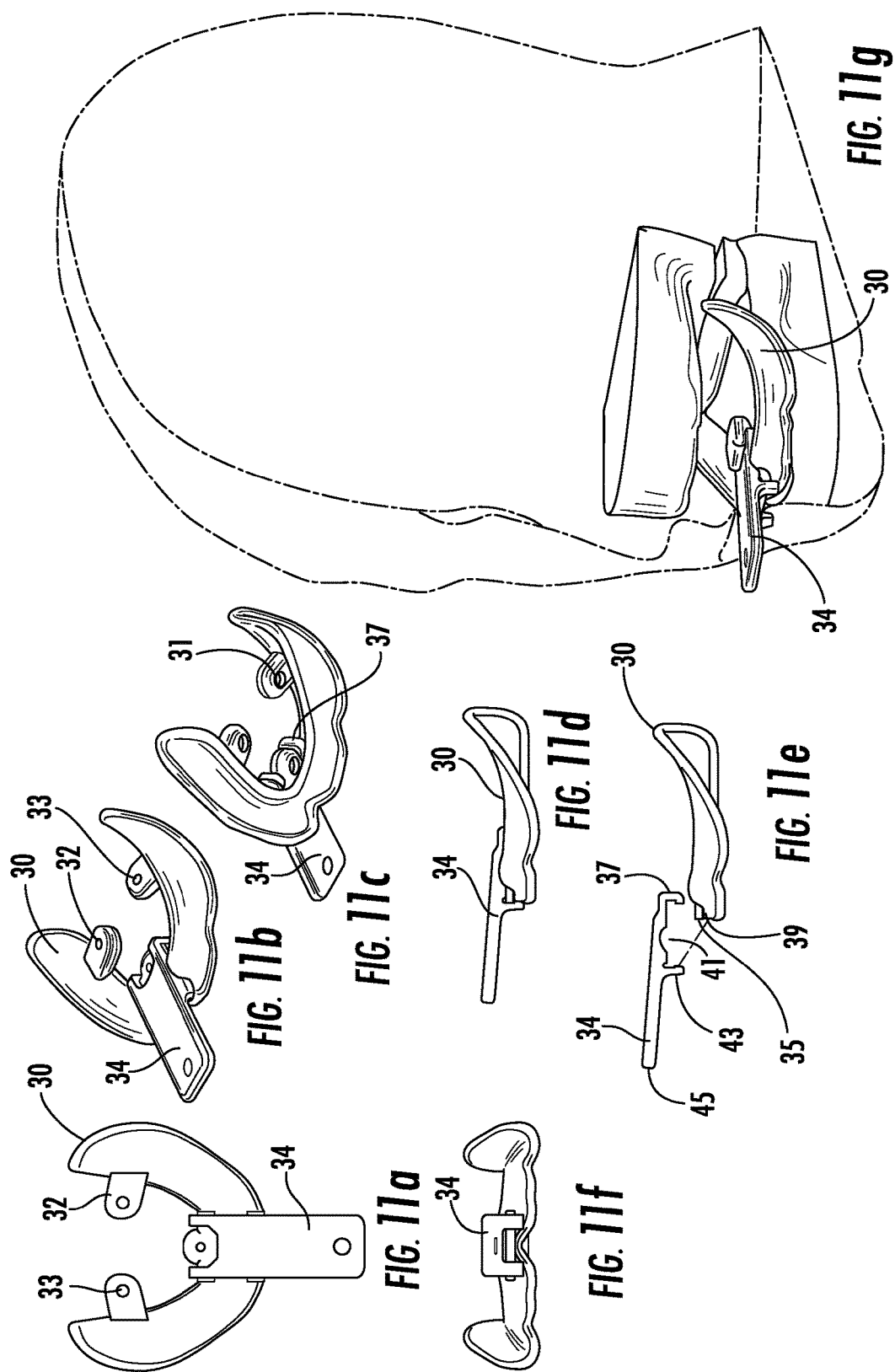

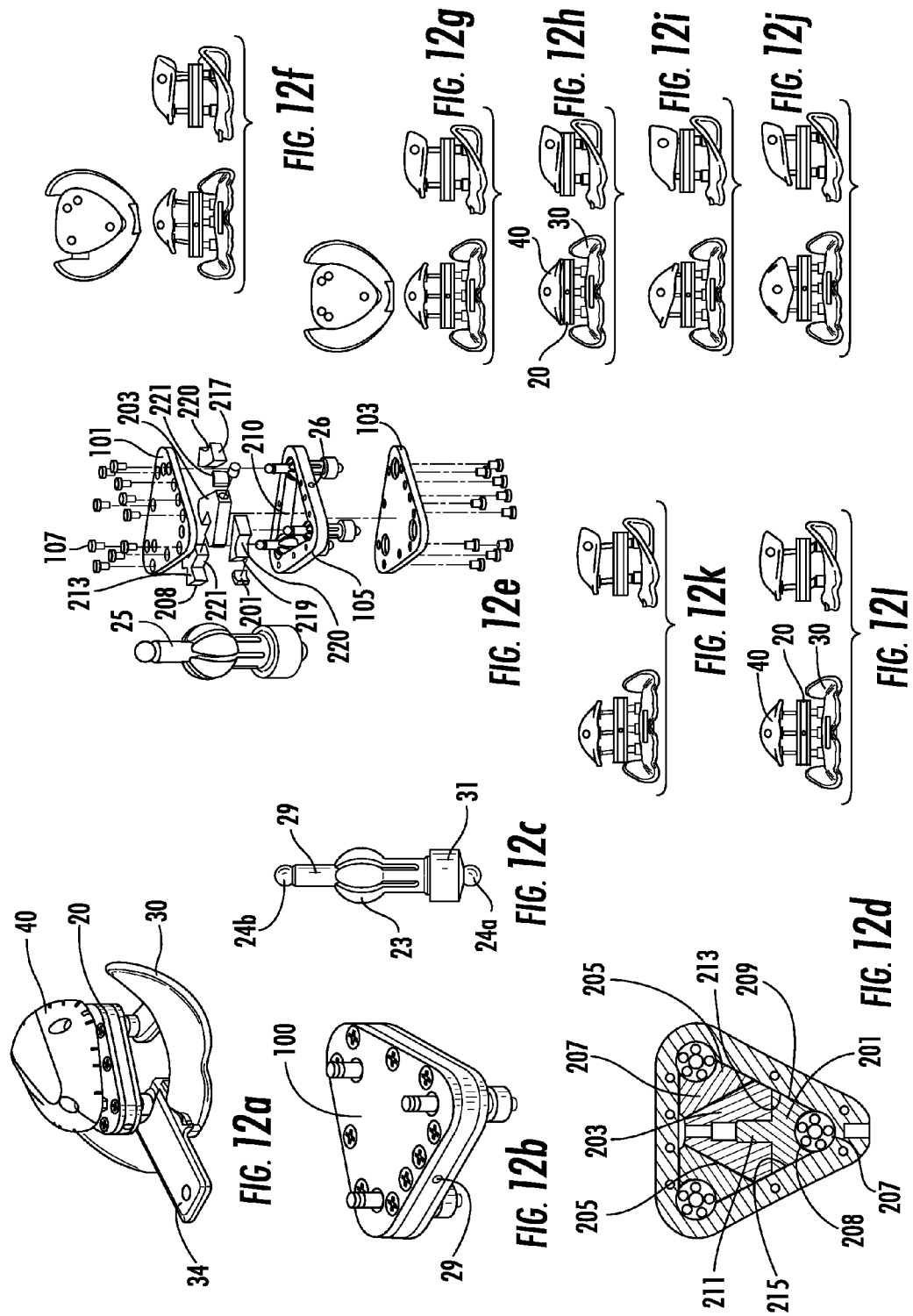

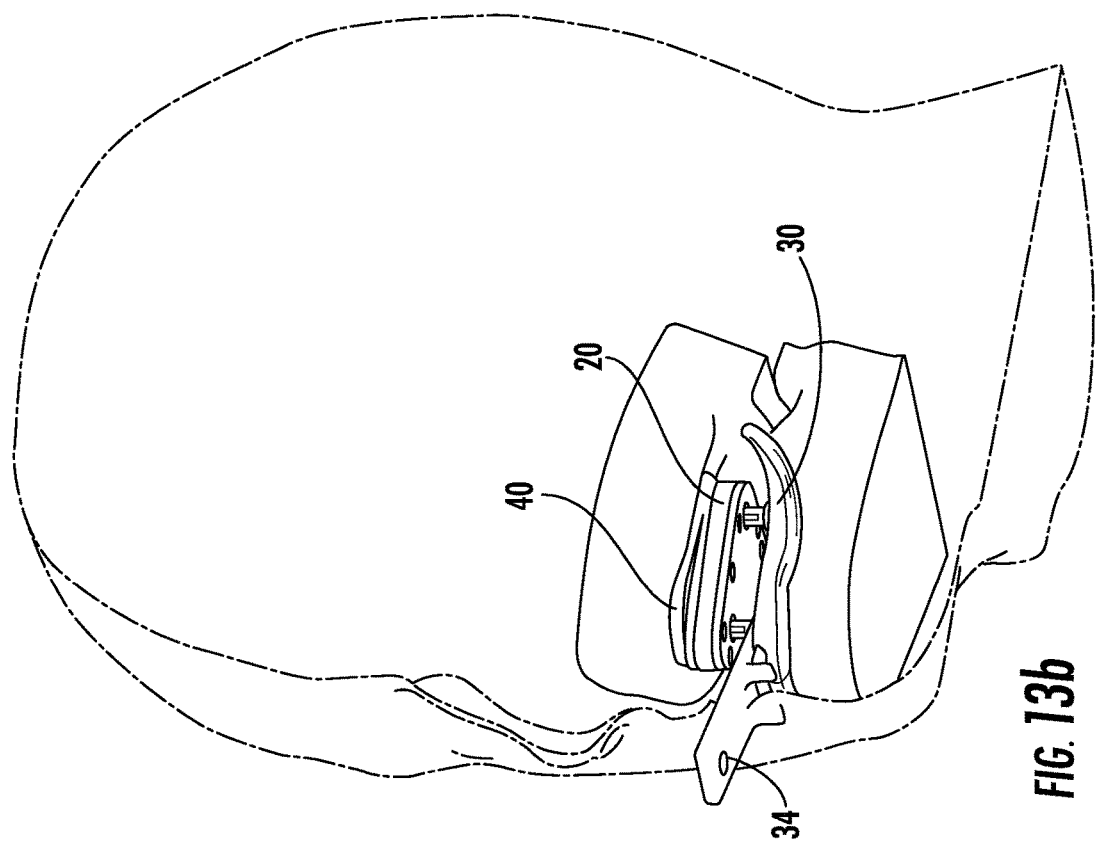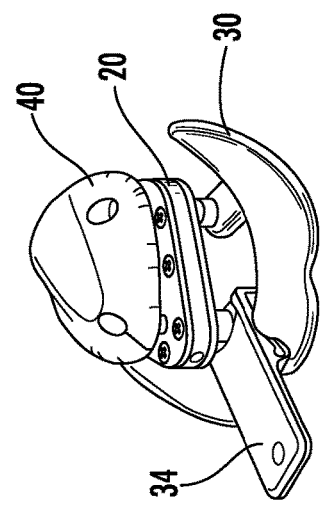

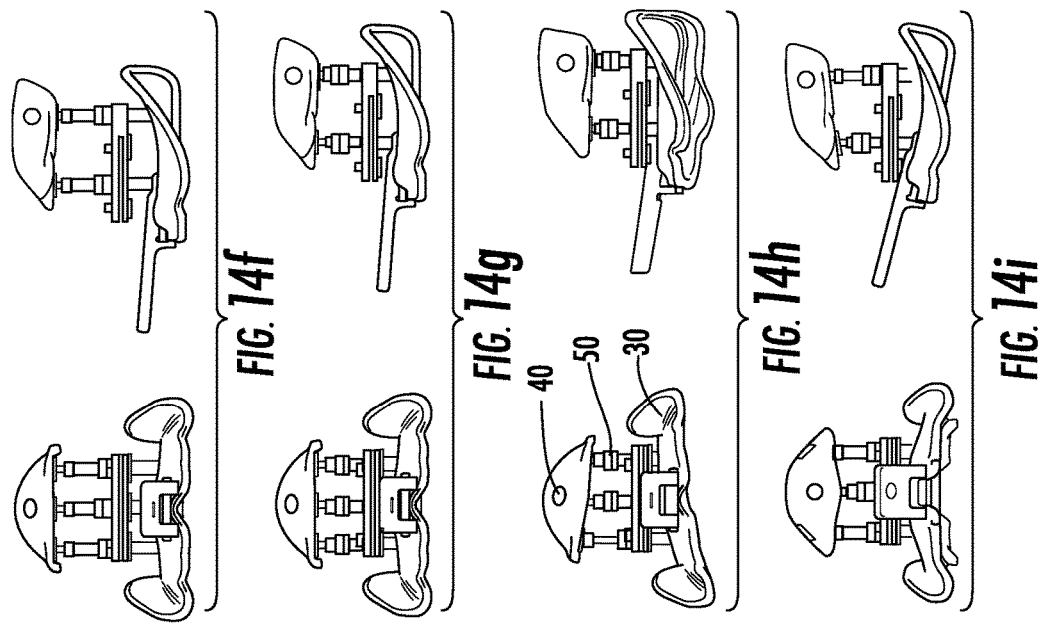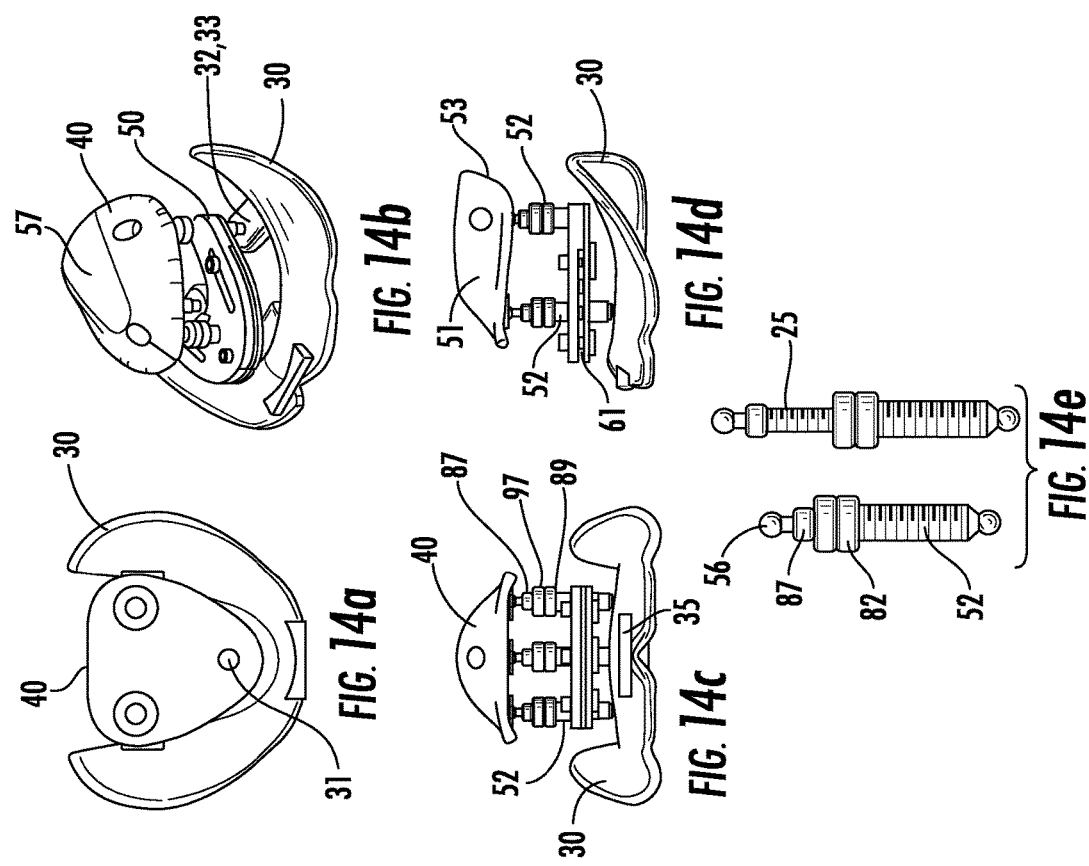

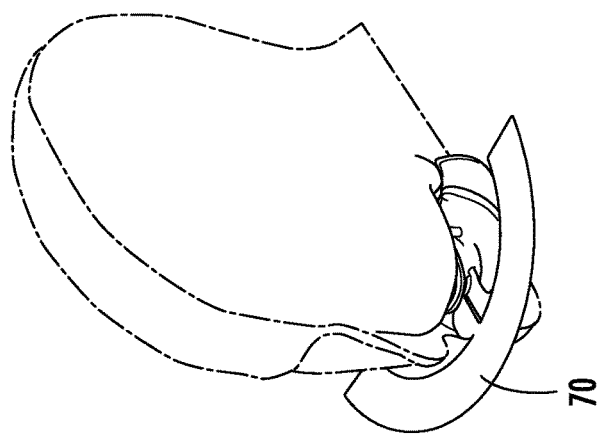
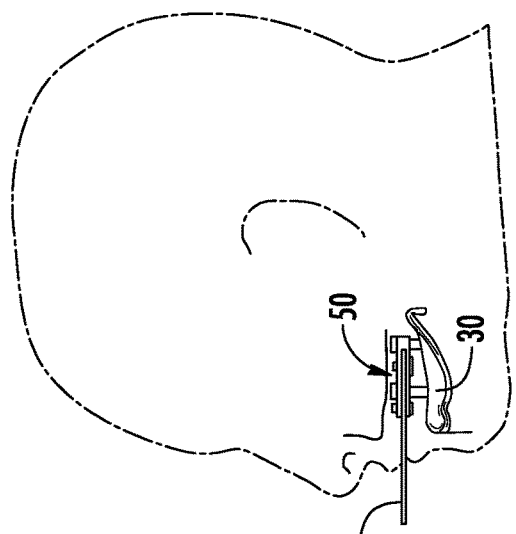
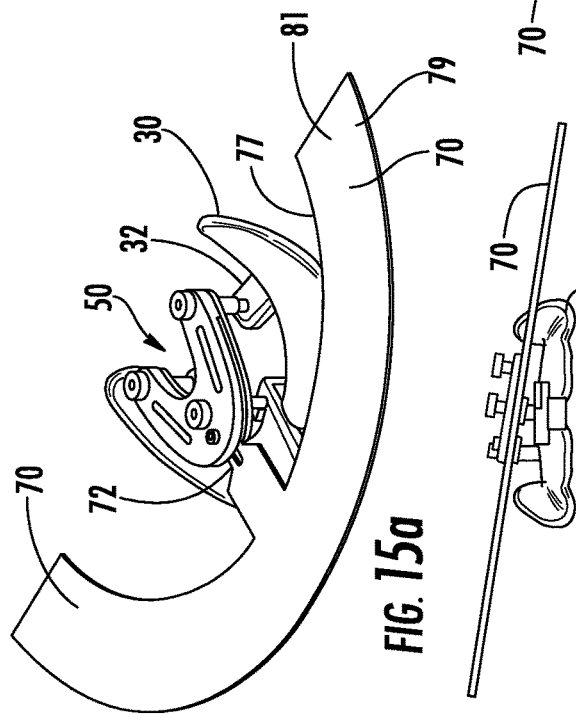
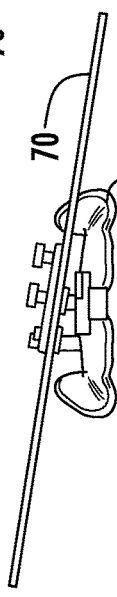
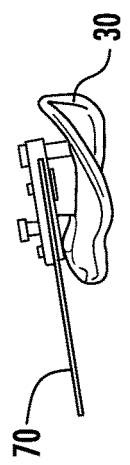

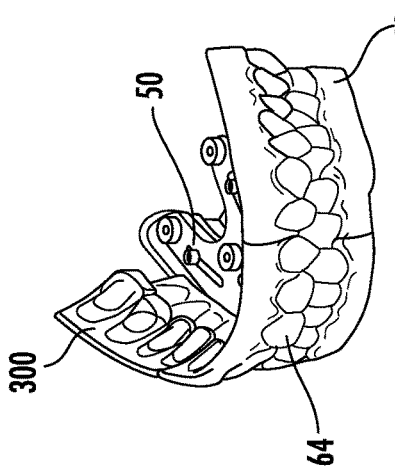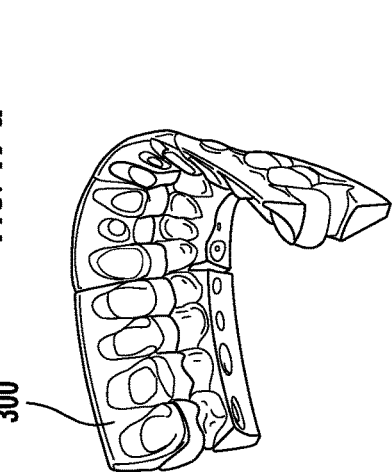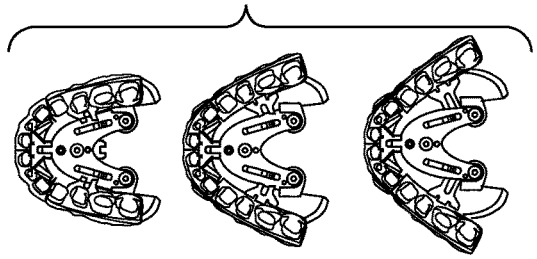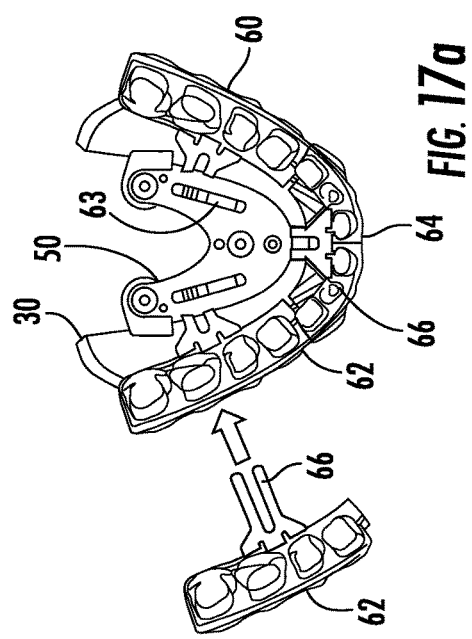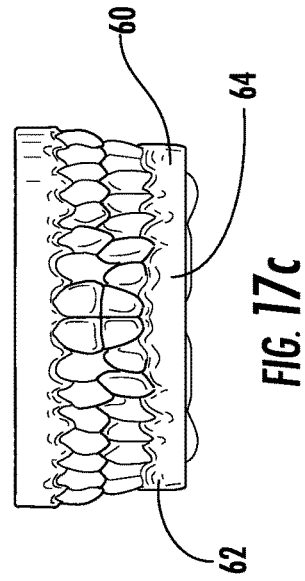

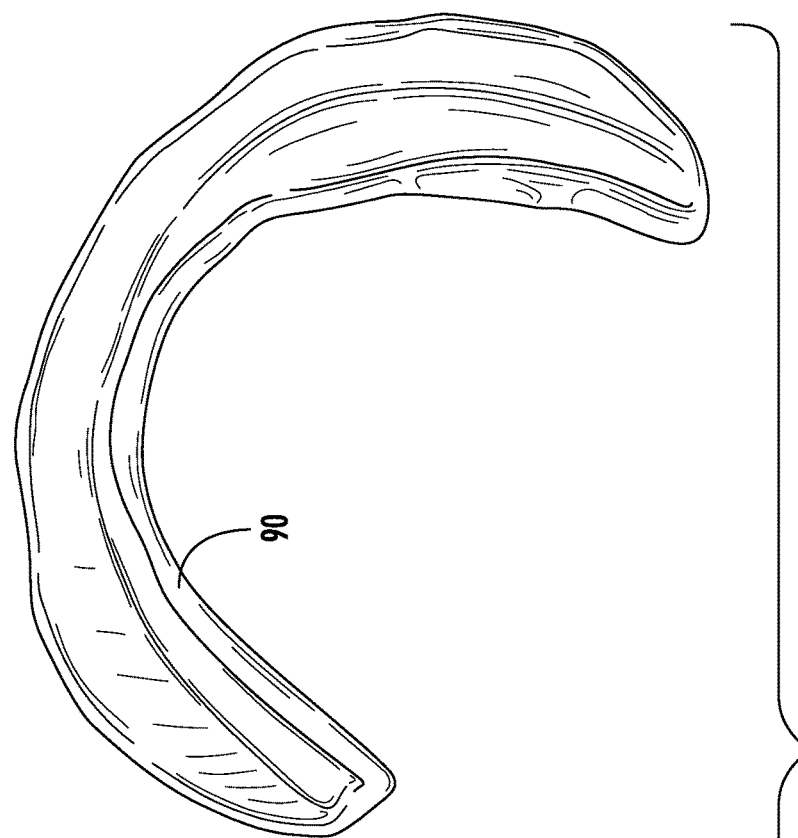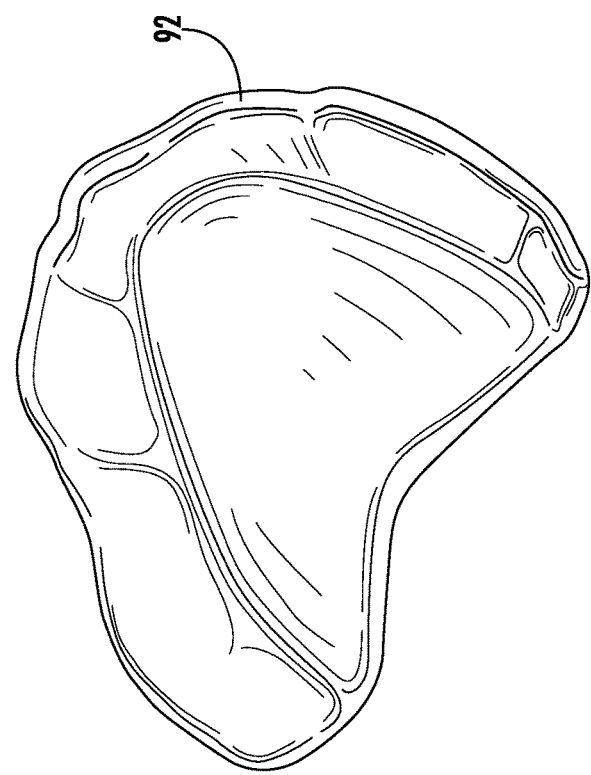
FIG. 21

COMPONENTS, SYSTEM AND METHOD FOR MAKING DENTURES IN A SINGLE VISIT

FIELD OF THE INVENTION

The present invention relates to individual components for use by a dentist to facilitate the creation of a model of a patient's mouth, one or more teeth therein, for use with forming replacements for one or more teeth for a patient, to an intra-mouth articulation device and a system to facilitate the creation of artificial teeth and teeth structures, and more specifically to an integrated dental system and method for forming dentures, partial dentures, implants and to aid in other dental procedures and products. Specifically, the present invention discloses a new device and associated components for use with an individual's mouth to provide an intra-oral dental articulator for use in forming dental impressions, one or more teeth, implants, etc. and even for the creation of a set of partial or complete dentures preferably during a single patient visit.

BACKGROUND OF THE INVENTION

As many individuals age they can become partially or completely edentulous i.e., they lose one or more teeth and, yet, gum tissue remains. This can be caused by a wide array of issues, including periodontal disease, tooth decay, improper nutrition, simple decay, developmental defects, genetic defects, and/or or trauma or other factors, presenting alone or in combination. When this occurs, individuals lose some or all of their teeth and should be fitted with one or more replacement teeth or a complete set of false teeth or bridges, implants, partial or full dentures, etc. (hereinafter often collectively referred to as "dentures" but it should be understood that the term is meant to be inclusive of everything and anything which a dentist may select to remediate a patient's tooth or teeth, i.e., within the normal range of dentistry) to replace those having been decayed or lost. To remediate and solve this issue, patients or individuals in need often get dentures, which are prosthetic, false (often acrylic or porcelain) teeth constructed to replace missing teeth. Removable, partial dentures are used when an individual has lost only some teeth, and a complete set of dentures, or dental implants, can be used when an individual is substantially or fully edentulous. The process, in the past, is done by a qualified and licensed dental practitioner and often requires more than a single dental appointment for first taking appropriate molds, sending the same to a lab, and then fitting the same into the patient's mouth. This is time consuming, expensive, possibly embarrassing to the patient until the dentures are provided, inconvenient to the patient, and often results in compromise in quality of end product. It is believed that a one-time, possibly single visit to the dentist's office, which will allow a fully or partially edentulous patient to go from a state of edentulousness to beautiful smile with a partial or complete set of dentures would be a boon to the patient, to the dentist, and to the dental manufacturer supplying the various components.

The present invention discloses the individual components, an integrated system, and a comprehensive method for preparing a set of dentures—partial or full—possibly in a single visit by using the patient's own mouth as the holding chamber or cavity for the molds and teeth to be used in the formation of dentures. In effect, the present invention provides a device for allowing the patient's own oral cavity to serve as the articulator for preparation of the dentures. Stated differently, by providing a new device, a "main frame" or articulator, which is used within the patient's mouth, dentures can be made to fit in a single visit to the dentist. The cost savings, time savings, comfort to the patient, the dentist's profitability, etc. are all maximized. This is a primary goal of the present invention.

Finished dentures are preferably composite or acrylic-molded teeth fit which are integrated into an acrylic set of gums which, as a unit, uppers and lowers, are then adhered or form fit into the mouth of a patient, fitting on the gums of the patient. These replacement teeth will be located precisely where the patient's original tooth or teeth have been lost, removed or destroyed. Of course, the new tooth or teeth are meant to match the patient's original tooth or teeth or to provide an enhanced set of teeth, all to provide a suitable smile with suitably shaped and colored teeth for the patient's mouth, complexion, smile lines, etc. For purposes of this disclosure, all types of dental procedures made possible by the present invention, namely full dentures, partial dentures, implant retention, and others, will often be hereinafter referred to collectively as "dentures."

DESCRIPTION OF PRIOR ART

Currently, to create and make a set of dentures, conventional articulators outside of the mouth are used. This can create errors in the measurement, angulation, occlusion, and placement of dentures if they do not precisely match the shape of the mouth once placed therein. The present invention aims to overcome this issue by presenting new components and a new system and method for creating a set of dentures using the patient's own mouth as the mechanical articulator, rather than reliance solely upon an external device. There is also a need for a set of dentures to be created for a patient in a quick, relatively inexpensive, and easy fashion, as opposed to a process which requires multiple dental office visits to complete. The present invention provides an accurate and quick system and method for making dentures in a single visit.

SUMMARY OF THE INVENTION

A system and method for creating a set of dentures for a patient by using the patient's mouth as the articulator is presented, comprising a customized lower dental tray for creating an impression of the patient's lower ridge of the mouth, a customized upper total or partial (herein the latter is often referred to as the palatal) dental tray for creating an impression of the patient's upper mouth portion including the palatal arch, and a main frame device for adjustably spacing and then locking in the separation and spacing of the impressions formed in the upper and lower trays while also serving as an artificial tooth holding device. The main frame, held between the inventive trays, allows for vertical adjustment of the spacing between the impressions formed by the trays and also for up to 6 degrees of freedom of the main frame with respect to the lower and upper or palatal tray while within the patient's mouth. The tooth holding device provides a frame for adjusting the vertical, horizontal as well as tilt of the trays, while allowing locking the same into place while within the patient's mouth.

The main frame coordinates with the other components. Dental impressions of the patient's mouth for the area of the same intended to obtain a denture are provided. Impression material can be placed into a dental tray and a negative impression formed. According to the invention, new and inventive lower and upper impression forming trays are each provided with a set of platforms, inwardly directed, which serve to magnetically hold the main frame in relation thereto. Columns or telescopic tubes or screws are vertically adjustable and then locked into place with respect to the patient's mouth and anatomy as well as with respect to the upper and lower trays. These telescopic screws or columns provide end tips or (ball-like surfaces) which magnetically connect, in a removable manner, to the platforms provided to the new impression trays. When adjusted, the trays are locked down with respect to the main frame held therebetween.

One or more sets of teeth or units of dentures comprised of a wax substrate and the actual and appropriate color, size and shape of tooth (teeth) sought to be created for the patient is provided. These units are securable to the main frame by a rearwardly extending fork-like connector passing into and held by a slit in the main frame. The position of the units of teeth are adjusted with relation thereto and then they, too, are locked in place. The trays, the frame and now the teeth are then used with an external articulator to complete the process since the relative orientation of the trays and the teeth with respect to one another are all fixed, all with respect to one another and as set by the patient's own mouth. The present invention allows for creation for an accurate set of dentures, using the patient's mouth as the articulator, and providing a system and method to do so in a single visit, thereby minimizing the time required for this process.

Basically, to prepare a set of dentures using the present invention, an impression is first taken of the upper and lower gum configurations. The mouth can be held open, if needed, using a set of retractors to pull the lips and cheeks apart, and providing free access to the gums. To make and take each impression, either a customized upper (full or partial) or a lower tray are provided which is first filled with soft, quickly curable, dental impression material. The impression material is preferably made of a flexible, formable material, capable of being shaped in the exact configuration of the ridge formed in the bottom and top of the endentulous patient (for purposes of ease of illustration a complete endentulous mouth is considered herein). Once the impression material is placed in each tray, the trays can be placed, preferably one at a time, into the mouth of a patient, on the upper and lower gums, respectively. The impression material will cure or harden (by mere passage of time, by a light curing device, etc.) once in place in the mouth, thereby creating a negative mold of the gums of the patient's mouth. In the preferred embodiment, the trays are coated with polyvinyl siloxane (hereinafter "PVS") for quickly and easily forming the impressions of the upper and lower gums. A suitable tray is used, much as in conventional dental molding or impression formation, with the proper shape, size, upper or lower, of course, being taken into consideration. However, according to the preferred embodiment of the invention, the impression forming trays are modified from that conventionally available for impressions, since they are provided with a set (preferably three) of inwardly directed supporting platforms for a frame, the frame serving to allow relative location of the upper and lower impression trays and for the artificial teeth to be formed by the present invention.

The upper and lower trays, consistent with the present invention, are quite similar to the conventionally available impression trays. However, it is an aspect of the present invention that the newly inventive dental impression trays used and provided herein be provided with an easily snappable, removably-coupled small handle, capable of attachment for controlling and directing the tray(s) into the desired location in the mouth and, yet, easily removed from the tray, after the tray, with the impression material cured, is removed from the mouth. The handle allows a dentist to properly position the trays into the mouth along the upper and lower gums and hold them in place so that the impression material can harden. The removable handles for the inventive trays facilitates the use of the trays in connection with the in-mouth articulation disclosed herein, as will be described.

Prior to the impressions or molds being taken, the vertical dimension of occlusion (the distance between the two dental arches) can be measured, as is conventional. This procedure is done according to conventional dental or industry standards—i.e., a pen dot is placed on the patient's tip of the nose and center of the chin, the patient relaxes by breathing in and out with their lips closed, and once relaxed, a ruler is used to measure the nose-to-chin distance, i.e., from one dot to the other.

The lower and inventive tray has a set of magnetically or otherwise connectable, radially, inwardly-directed platform support areas integrated therein, which allow the connection points, balls, end points of columns, or telescopic screws with locating nubs etc. of a frame device to be secured or connected thereto.

The main frame is preferably formed of metal and primarily comprises a horizontally-extending plate with a plurality of, preferably three, vertically extendible and compressible columns (or in the preferred embodiment, telescopic screw columns) held therein and passing therethrough, each column having up to six degrees of freedom about the plane defined by the plate of the main frame. The lower tray, with the main frame superimposed, the latter's columns or screw/balls/ends being magnetically secured to the horizontal platforms of the lower tray, are assembled together outside of the patient's mouth. While the main frame is securable (by magnetics) yet removably connected to the lower tray, with the lower ends of the columns or telescopic screws being held upon the magnetically attaching platforms, an upper palatal piece or partial or full tray is placed above and on top of the main frame, the palatal piece or upper impression tray having inwardly directed platforms, too, preferably three in number, which magnetically and temporarily secure to the upper ends of the extendible and compressible columns or those of the telescopic screws with balls, ends, of the telescopic screws of the main frame. The secured-through columns or telescopic screws forming columns of the main frame have upper projections and lower projections (preferably in the shape of balls) which are magnetically captured by the inwardly directed, magnetic platforms of the lower tray and the palatal tray. The columns or telescopic screws, between the upper and lower trays, are vertically closed or compressible between the upper palatal arch of the patient and the lower gum of the patient, when the three parts of the system are reinserted into the patient's mouth and the patient performs a conventional "bite." The mouth is filled with the lower tray with formed lower gum impression and the main frame thereon (its columns resting on the platforms of the lower tray) and the palatal piece or upper tray resting and magnetically secured on the upper projections of the columns or telescopic screws of the main frame. The full upper tray, placed aside for much of the procedure, could be used but the smaller profile palatal tray, a new customized component is desirably used. It is believed that the smaller palatal piece or tray is desired because of the degree of room, or absence of space, within the patient's mouth. Too much foreign material in the patient's mouth can lead to discomfort. The palatal tray is similar to the upper tray but does not have a component for forming the negative impression of the upper gums of the patient. Rather, it is merely a generic, yet sized, piece (like a convex curved, smooth walled and curved pointed, triangularly-shaped, piece) which comes into contact with the roof or upper arch of the mouth. The full upper or preferably palatal tray, consistent with the present invention, is also provided with inwardly directed, preferably metallic or magnetic support platforms for sitting atop the balls, ends, projections of the columns or telescopic screws of the main frame. The palatal piece is preferably smaller than the full upper as it is not designed to create a mold of the gums for teeth, but merely to rest below the upper or roof of the mouth of the patient so as to provide proper measurement of the vertical opening of the mouth while the main frame, with the lower tray and the negative of the patient's lower mouth, is placed therein.

The compressible columns (or telescopic screws) of the main frame, which can be caused to expand or retract in vertical dimension when one is moved within the telescopic body of the other are associated with and pass through the horizontal plane of the main frame. The columns or telescopic screws are preferably provided, on both ends, with small, ball-like projections, of metal or magnets adapted to snap into and be securely yet removably connected to the corresponding magnetic platforms or "sockets" on the upper or palatal tray and the lower tray. Magnetic projections or ball-like magnets of the distal ends of the columns or telescopic screws, couple to the small horizontal platforms of the palatal tray and the lower tray and, yet, the columns are vertically compressible between the platforms either by interior springs which allow the columns to shrink when compressed or by simple screwing of one telescopic screw within the outer telescopic screw. Also, the columns or screws are held within the main frame but pass therethrough and are movable or pivotable in up to six degrees of freedom. Stated differently, the columns or telescopic screws are securely yet pivotally held between their ball ends in the main frame but pivot about those central holding locations or pivot points so that the balls or projections can be placed on the respective platforms of the trays even if the upper or palatal tray is not exactly aligned and superimposed over the platforms of the lower tray.

The platforms and the projections, magnetically coupled to one another, allow the trays to be removably coupled to the main frame, but held securely in position while all is replaced back into the patient's mouth and selectively removed. The coupling of the magnets or ferromagnetic material of the platforms of the trays and the metallic or magnetic projections of the columns/screws allows the platforms of the trays (palatal and lower) to be snapped onto the projections of the columns (or the magnetic balls) and allows the trays and main frame to be held and placed into the patient's mouth as a unit. The mechanical interaction also allows for movement, vertically, forwardly, side to side, etc. of the trays within the patient's mouth and relative to the other tray until the patient and dentist is comfortable with the relative location and the fit and occlusion desired and required between upper or palatal tray and the lower tray, the latter with the negative mold secured therein (which fits over the ridge of the gums of the patient).

The compressible and expandable spring-biased or screw-threaded, columns or screws passing through the main frame, are preferably configured to move up or down, forwardly and rearwardly, and side to side, with respect to a central pivot point of each column/telescopic screw, all relative to the palatal tray and the lower tray, while having the columns or telescopic screws held to the supporting platforms of the trays. Thus, the vertical dimension and angle of the upper, palatal tray can be moved relative to that of the lower tray, all to match the height, space, orientation, and angle of the interior cavity of the patient's mouth all while within the patient's mouth. Additional impression material can be placed on top of the upper, palatal tray, i.e., on the side not in contact with the projections or ball ends of the columns or screws of the main frame, so as to get an additional negative mold of the upper cavity/arch of the mouth as well. This can be used later, as will the impression formed by the lower tray, to create stone molds of the patients mouth and then custom trays, to be used with the frame, the upper or palatal and lower trays and the artificial teeth, all to create dentures for the patient.

When the main frame is placed into the patient's mouth, with the lower tray having the cured lower gum impression therein and the palatal tray above the main frame, all secured between the ball ends of the columns/telescopic screws, the cured, negative mold created in the lower tray should allow the tray to sit comfortably on the lower gums (after-all the mold matches that of the patient's gums) thereby allowing the upper, palatal tray to move into place into the roof of the mouth in accordance with the curvature and location of the upper arch of the mouth.

Once the main frame, lower tray and upper or palatal tray are located within the mouth, and height and relative side, forward, occlusion dimensions satisfied (either by compressing the mouth against the spring bias of the columns or by manually adjusting the telescopic screw threads) the dentist can "lock" in place the angle of the columns or telescopic screws, the amount of their vertical spread, and thereby lock in place the relative location and orientation of the lower tray and its impression material and the upper or palatal tray, along with the main frame therebetween. When the upper palatal tray, the lower tray, and thus also the columns/telescopic screws on the main frame, are in the proper position relative to the lower tray with the cured impression material therein, the compressible columns or telescopic screws (simple telescoping columns are provided with springs contained therein or internal threaded outer screws receive externally threaded inner screws) all can be held firmly in place by use of a small Allen wrench adapted to mate with a set screw within the base of the main frame. Mechanically, tightening the set screw will cause mechanical components within the main frame to "lock down" the movement of the columns or the telescopic screws, vertically and about the degrees of freedom. When the set screw is turned, it bears against a movable pressure plate which in turn is pushed towards a first column, which also pushes against one or more sliding plates. The sliding plates then push towards the other two columns, forcing each one into place with no capacity to continue to move. This serves to lock the columns of the main frame in place, thus holding the lower and upper palatal trays in place as well. Alternatively, the telescopic screws can be locked in place after they are accurately adjusted.

The main frame is preferably provided with multiple locking set screws and at alternative locations so that any one can be conveniently reached for locking the components in location using the small Allen wrench (passing between the patient's lips) from the front (where no teeth are present) or from either side, in the case where a patient has front teeth and only needs partial side dentures. This first embodiment of the main frame is basically an equilateral triangle (with rounded corners) in top plan view and it is thus able to be placed with the support platforms of the upper or palatal tray thereon and upon the platforms of the lower tray, independent of which side of the main frame faces forwardly. The platforms of the lower tray and the palatal tray are at or near the corners of the corresponding and virtual equilateral triangle formed by the platforms so that the projections of the columns (or the magnetic ball ends of the telescopic screws) one at each corner of the main frame, superimpose over and are aligned with the platforms. Once the main frame is locked, it, along with the palatal tray and the lower tray can be removed from the mouth. Those trays can be removed and reapplied to the main frame, as needed in the procedure.

In the embodiment disclosed with telescopic screws for adjusting the distance from the main frame to the platforms on the palatal tray and the distance from the main frame to the platforms of the lower tray, a turning wheel surrounding the external threads of the outside telescopic screws lock the distances between the platforms, upon which the ball surfaces of the screws rest and are magnetically held.

Thus, while the main frame and lower tray and upper or palatal trays, having been removably connected by means of attractive magnets on the projecting ends of the columns or telescopic screws of the main frame and the inwardly directed platforms of the trays, are in the mouth of a patient, a small Allen wrench can be used to turn the set screw within the main frame and lock the columns (or the telescopic screws of the telescopic screw embodiment) and thus lock the trays in relative location, spatially and dimensionally, by the mechanisms referred to and briefly described above. Upon securement of the columns and telescopic screws and ideal positioning of the trays with respect to the main frame, the first main frame and trays can be removed from the patient's mouth.

While the embodiment of the present invention described above may utilize first main frame and second main frame in combination to produce a set of new dentures, it is preferably envisioned that the system and method performed by the present invention can be done completely and with the same success and positive results using only the preferred, second main frame for all steps. Thus, both embodiments are disclosed herein. The preferred embodiment of the present invention comprises use solely of second main frame. Accordingly, most of the description herein as to the method will detail use of only second main frame and without much emphasis made on the first described main frame, except as to its structure. However, it and other embodiments of the main frame are contemplated and considered within the scope of the present invention. The originally disclosed main frame, element 20, can be adopted and adapted for use like the presently preferred main frame II, element 50.

Second main frame 50 is preferably metallic, arc-shaped and defined by a primary horizontal plane, with three of the height adjustable columns (referred to as telescopic screws) secured thereto. The horizontal plane is slit to allow for the selective securement and removal of an occlusal plane (described hereinafter) and sets of teeth held in wax which will become the actual artificial teeth of the patient. The telescopic screws or columns, briefly described above, are located at the rear ends of the arc-shaped horizontal plane and at the central point of curvature of the same. Those columns or telescopic screws can be vertically adjusted and then locked. The columns or telescopic screws are provided with ferromagnetic or magnetic attractive ends, preferably in the shape of small balls, which will be captured, held, yet are removable, from the inwardly extending platforms of the upper or palatal tray and the lower tray.

Each telescopic screw is provided with magnetic ends which are adapted to connect to a complete lower impression-providing tray, a complete upper tray, and/or an upper, partial or palatal tray. Each telescopic screw or column is preferably provided with one or two locking nuts. The columns are telescopically constructed, one smaller cylinder with external screw threads incrementally turning into and extending out of and thus decreasing and increasing, respectively, the overall length of the column within the outer cylinder having internal screw threads. Similarly, the outer cylinder of the column has exterior screw threads which mate with apertures and screw threads of the main frame. Thus, each telescopic screw or column's length can be adjusted and the distance from the top of the main frame to the ends (magnetic balls) can be adjusted. Thus, the distance between the lower tray and the upper/palatal tray is adjustable as is the location of the main frame in between that distance. This second yet preferred main frame is provided with a slot along its horizontal axis in which various fork-shaped pieces, connecting to artificial teeth, can be slidingly adjusted and held. The first main frame can be similarly constructed although not shown in the present drawings.

To achieve proper placement of second main frame within the mouth, an occlussal plane device is provided and can be used. This device is a thin, flat, curved, preferably metal tool, which is arc-shaped and will surround the patient's face, when its rearwardly extending fork is captured and held in the slit of the second or preferred main frame. This allows the dentist to ensure dental principals are maintained, i.e., for example, relative horizontal location of the main frame across the patient's face, facilitating alignment of the nose, the lower ends of the ears, the patient's eyes, across the adjustment of the main frame's location and height. The occlusal plane device is positioned to align parallel to the eyes, nose, and ala tragus of the patient, ensuring that the second main frame has been placed in the proper alignment so that the installed dentures will be straight, as desired, and not crooked. This is all done consistent with standard dental principles. Using the locking and turning nuts of the columns of the second main frame, the columns can be raised or lowered so that the slit is moved to align the occlusal plane with the eyes and ala tragus. Once height and angulation front to back and side to side is achieved, the locking and turning screws of the telescopic screws of this main frame are secured and the device, main frame, lower tray and upper or palatal tray can be removed from the patient's mouth.

Teeth are then inserted and held to the main frame. These newly inventive teeth are formed of at least one type of wax as a substrate for the acrylic or porcelain teeth. The teeth are supported by metal forks which allow the teeth, as units, to be placed upon and secured in the main frame. Once located, the teeth are locked in place, vis a vis the main frame. the device is then removed from the patient's mouth, i.e., lower impression tray, main frame and the palatal tray, for creating the dentures.

Next, a mechanical and conventional articulator is used for forming the basic and often precise positive of the patient's mouth. Once removed from the mouth, the lower tray can be removed from the preferred or second main frame. The upper and lower negative impressions of the lower gum and mouth structure and the palatal arch and its gum structure, secured in their respective trays, are then poured with dental stone. The dental stone creates a positive impression of the patient's mouth, as it will form within and around the negative impression made by the molded and then cured impression material in the trays. Then custom trays are formed from the stone models.

A standard, mechanical, external-to-the-mouth, dental articulator can be used as a holding unit for the stone models. Quick setting dental plaster can then be placed on the bottom (and the top) of the conventional articulator; the lower stone model just formed being still attached to the lower impression tray. It is placed on the conventional articulator, holding it until the quick-set plaster is dry. Once the stone model is made, the lower tray and upper palatal tray can be reconnected to the main frame so that the proper height of the overall stone model, i.e., the distance between the top of the upper palatal tray and the bottom of the lower tray, can be determined. Quick setting dental plaster can then be poured on top of the upper stone model to fill in the gap between the top of the upper stone model and the bottom of the top of the conventional articulator. This serves to hold all pieces in place at the correct distances corresponding to that of the patient's mouth as determined by the patient's upper and lower gums, their separation, all as replicated by the use of the trays, their impressions, and the main frame, as adjusted. If the configuration of the upper, lower, and upper palatal tray—each with molded impression material—match the stone models exactly, a perfect reconstruction of the mouth has been made. This will facilitate the construction of the dentures.

After the stone model is complete, the impression material can be removed from the trays and the stone models. Light-cured material can be placed over the upper and lower stone models which are now positive replicas of the patient's mouth—and maneuvered into place to form a custom impression-like tray (hereinafter referred to as the "custom trays") of the top and bottom of the mouth, in the same manner that the original impression material was used. When heated with light or otherwise cured, the custom trays will be set in place and form negatives of the patient's mouth, adapted to fit perfectly onto the stone models and thus into the patient's mouth itself. The custom trays can be placed onto and into the stone models and placed back into the conventional articulator, adjacent to the lower and upper palatal tray and the second main frame.

The next steps relate to actual formation and arrangement of the teeth which form the dentures. Sets of artificial teeth, which will be used for the dentures, can be used. These are commercially available, now, in proper shapes for the dentures to be formed, color, and size. According to the present invention, these acrylic teeth are pre-set in a wax substrate, which will act temporarily as the patient's gums. When suitably but slightly heated (preferably by means of placing the teeth in or under a stream of warm water) the wax will become malleable and able to be formed to the general shape and configuration of the patient's mouth and gums and the arch of the mouth. The teeth, preferably provided according to the present invention, are integrated units of upper and lower pairs of twelve total teeth, e.g., six upper front, six lower front as a single unit; four upper right and four lower right, as a second unit; and four upper left and four lower left, as a third unit. The teeth in these "units" of teeth are secured in a two-wax composition. The first wax composition allows the units to be molded into the general curvature of the patient's mouth. The second wax composition will be described and its function, hereinafter. The wax serves to hold the teeth in relative orientation with respect to the other adjacent teeth in the same row (upper and lower) in the unit and with respect to upper and lower teeth of the same unit. The wax serves, at least temporarily, as the gums into which the patient's teeth will be held and located. The wax sets of teeth or units of waxed-together teeth are each provided with a rearwardly directed fork. It is thin and preferably plastic or metallic. The tines of the fork have been slid into and retained by the slit of the second-described, now preferred, main frame. The teeth units can be attached to the main frame by the rearwardly extending forks integrated with the teeth, by the wax composition. The forks extend from the rear of the wax holding the units together, i.e., the side of the units opposite to the front of the teeth. The forks slide into the slit of the main frame and allow for sliding placement into and out of, forwardly and rearwardly of the teeth units along the horizontal slit in the second, preferred main frame. When second or preferred main frame is placed back into the patient's mouth along with lower tray and upper palatal tray, the sets or units of teeth in the wax substrate can be first heated in hot water, and then the forks slid into the slit of the main frame. The tines of the forks will surround movable connector posts which slide along and can be locked into location along the horizontal slit of the main frame within opposed slots. These connectors have a locking screw which, when tightened, locate the units of teeth along the longitudinal slit of the main frame.

Once the custom trays are re-connected to the stone models in the conventional articulator, the lower and upper palatal trays, and the second main frame now having the units of teeth roughly adjusted on the main frame, commercially available baseplate dental wax can be heated up and attached to the custom trays to connect the impressions of the custom trays (upper and lower) to the wax substrate attached to the units or sets of teeth (already connected by fork-like connector clips to second main frame) so as to leave no interstitial tooth to adjacent tooth gaps. This dental baseplate wax will also become malleable once heated, and it is adapted to be inserted along any ridges or troughs in the custom trays and to seal together the teeth to the respective upper or palatal tray and lower trays. The combination of wax and the teeth units, with the custom trays will create a positive mold of the gums of the patient so as to perfectly match that patient's mouth. This will provide a dentist with the correct height and depth of the dentures so the teeth are properly positioned and orientated. This step will be performed for both the lower and upper or palatal custom impression trays.

Once the base-plate wax has cooled and become set into place, the units or sets of teeth (still held in the main frame) will be connected by baseplate wax to the custom trays. The teeth can then be unsecured from the main frame, and the custom trays can be removed from the original impression trays. This will leave an upper mouth impression and a lower mouth impression, each made of the stone model, impression of the custom tray, base-plate wax, and teeth sets. Second main frame is no longer required.

The resultant components are then dipped into hot water (but at a lower temperature than was required to melt the base-plate wax), allowing the rear forks of the teeth units to be easily removed from the rear of the teeth and melting the wax substrate of the teeth units but not the connecting base-plate wax. This also separates the top teeth from the bottom but, of course, the top teeth are now secured to the upper custom tray and the bottom teeth secured to the lower custom tray. Thus, upon placing the models into water of that certain temperature, the wax substrate for the teeth and connector clips previously connected to the teeth will melt away, while the base-plate dental wax will remain connected to the teeth and custom trays. This will leave just the upper and lower denture molds—the upper teeth separated from the lower teeth.

Once the stone model and wax molding is complete, conventional dental lab work can be provided, either on site at the dental office, or sent to a stand-alone dental lab. The custom trays and attached by baseplate wax acrylic teeth, can be turned into a final set of dentures, using basic dental principles. The same acrylic teeth of the teeth units, used and adjusted in the main frame are used for the final set of dentures for a patient, with the wax molding of the custom trays (resembling the gums) replaced with acrylic. Using the technique disclosed herein, a set of dentures can be made with a perfectly molded set of "gums" which match the orientation, angle, curvature, and shape of the particular patient's mouth, so that the dentures will fit the mouth as if they were the patients' actual teeth. Additionally, the entire system and method described above can be completed in a single visit.

It is an important aspect of the present invention that the units and teeth of the units used herein are actually the final teeth of the dentures ultimately provided to the patient for use.

This and other aspects of the present invention are disclosed herein. The present invention comprises a set of new dental components, a new system and a new method for forming a set of dentures, primarily by using the patient's mouth as the intra-oral articulator. The present invention comprises a new upper and/or partial palatal and a lower impression forming trays, formed with inwardly directed support platforms. A main frame is also provided which is situated between the platforms of the upper tray (or a palatal or partial tray) and the lower tray. The main frame comprises a set of vertically adjustable columns or telescopic screws (preferably three) which are supported by and upon the platforms of the upper and the lower impression trays. The platforms and the ends of the columns/telescopic screws, the latter preferably provided with round ends or ball surfaces, are magnetically secured yet separable from the main frame with simple mechanical/manual force applied to one another.

BRIEF DESCRIPTION OF THE DRAWINGS

FIGS. 11 (a-f) are (a) bottom plan, (b) front and top perspective, (c) bottom and rear perspective, (d) side perspective, (e) exploded side perspective, and (f) front elevational views of the lower impression tray and handle used in connection with the present invention, the handle being used for positioning the lower tray in relative location in the mouth for taking an impression;

FIG. 11(g) is a rear, side and perspective view of the lower tray and handle disclosed in FIGS. 11 (a-f) as would be seen being placed in the mouth of an edentulous user;

FIG. 12a is a front, top and side perspective view of the first main frame magnetically connected to the lower impression tray and with an upper palatal tray, with the removable handle connected to the lower tray;

FIG. 12b are multiple illustrations showing top, partial sectional, side, rear, and top perspective views of first main frame as seen in FIGS. 1-3 prior to connection to lower, upper or palatal trays;

FIG. 12c are multiple illustrations of the telescopic columns used in the main frame of FIGS. 1-3 with ball pivots, and, specifically, show the top, side cross-sectional view, side, and top perspective views of the same, with the columns having been removed from the main frame;

FIG. 12d is a top plan view of the internal structure of first main frame (with the top lid or plate removed) showing the bores for the set screws, pressure plates, and distributor plates used to tighten and lock the telescopic columns about their spherical surfaces in place at the desired orientations;

FIG. 12e is an exploded side perspective view of the components of first main frame;

FIGS. 12(f-l) show top, front and side perspective views of the first main frame with lower impression tray and upper palatal tray connected thereto, showing the potential adjusted position (or slight rotational change) of the upper palatal tray, also showing the movement of the telescopic columns with respect to the main frame supporting the palatal tray and the telescopic columns with six degrees of freedom allowing for the same prior to being locked in place. These figures show a twist of the palatal tray. FIG. 12(g) is a bottom, front and side view of the maximum vertical extension of the palatal tray, FIG. 12(h) is a front and side view of the minimum height of the palatal tray, FIG. 12(i) shows the tilting of the same to one side, FIG. 12(j) shows the tilting of the palatal tray forwardly and backwardly, FIG. 12(k) shows the shift of the palatal tray towards the left side, and FIG. 12(l) shows the shift of the palatal tray forwardly, and all with respect to the lower tray while the main frame is held horizontal;

FIG. 13a is a top, side and front perspective view of first main frame shown located on the lower impression tray, and with the palatal tray secured thereto;

FIG. 13b is a bottom, side and front perspective view of the first main frame with lower impression tray and upper palatal tray as seen in FIG. 13a as would be placed into the mouth of a user with molded impression material on the lower tray and having the handle releasably connected thereto, the patient shown biting on the same and the set screw at the front of the main frame being ready for locking all in place;

FIG. 14a is a top plan view of the second or preferred embodiment of the main frame as magnetically connected to the lower tray and the upper palatal tray;

FIG. 14b is a front, side and above perspective view of second main frame magnetically connected to lower tray (handle removed) and upper palatal tray as seen in FIG. 14a;

FIG. 14c is a front elevational view of the second main frame magnetically connected to lower impression tray and upper palatal tray as seen in FIG. 14b;

FIG. 14d is a side elevational view of second main frame connected to lower impression tray and upper palatal tray as seen in FIG. 14b;

FIG. 14e are front elevational views of the telescopic columns or telescopic screw members (fully contracted and expanded) of the second main frame, separated therefrom, the columns provided with knurled sections and a locking nut which aid in the mechanical adjustment and securement of the height of the columns or telescopic screws and their relative positions with respect to the upper palatal tray and the lower impression tray, when the ends or "balls" of the telescopic screw members are attached to the platforms of the trays;

FIGS. 14(f-i) show various front and side/perspective views of the second main frame with lower tray and upper palatal tray connected thereto, showing the potential relative movement of the upper palatal tray relative to the lower tray, in terms of height adjustment and side tilt as well as forward/back tilting.

FIG. 15a is a top, front perspective view of the second main frame connected to the supporting platforms of the lower impression tray and with an occlusal planar device attached to the front of the main frame by a fork connector clip, the occlusal plane used to provide the dentist with a broad surface to ensure proper alignment of the dentures with the patient's mouth and face (according to standard dental principles);

FIG. 15b is a front elevational view of the main frame with occlusal plane shown in FIG. 15a, showing the plane at an angle and thus the screw columns are "in need" of adjusting to level the occlusal plane across the patient's face, according to standard dental principles;

FIG. 15c is a side perspective view of the main frame with occlusal plane shown in FIG. 15a, showing the plane at an angle of decline from front to rear and thus in seeming need of raising the two rear columns or screws in the main frame, i.e., by extending the overall length of the telescopic screws towards the rear of the mouth;

FIG. 15d is a side perspective view of the main frame with occlusal plane shown in FIG. 15a after front-to-back and side-to-side leveling has occurred, by adjusting the telescopic screws of the main frame;

FIG. 15e is a top, front perspective and partial cross sectional view of the second main frame with occlusal plane shown in FIG. 15a as would be placed into the mouth of a user;

FIG. 17a is an exploded view of the main frame having three units connected thereto—a front and two side units or sets of teeth for use with the present invention, all forks of the same being held within the horizontal slit of the main frame;

FIG. 17b shows various top views of the main frame connected with three sets of teeth or units as seen in FIG. 17a, showing various curvatures and locations of the units, as can be adjusted depending upon the patient's mouth and gums, by sliding location of the forks of the units in the slit of the main frame;

FIG. 17c is a front and perspective view of main frame supplied with three sets of teeth or units, as shown in FIG. 17a;

FIG. 17d is a top, side and front perspective view of the main frame having supplied thereto the three sets of teeth or units as seen in FIG. 17a;

FIG. 17e is a rear, side and top perspective view of the three sets of teeth, with second main frame and the connectors having been removed therefrom, for ease of understanding;

FIG. 21 is a bottom, rear and top perspective view and top and rear perspective view of the custom trays, respectively, i.e., the flipping over of the trays shown in FIG. 20;

DETAILED DESCRIPTION OF THE DRAWINGS AND THE PREFERRED EMBODIMENTS

Figure 1:
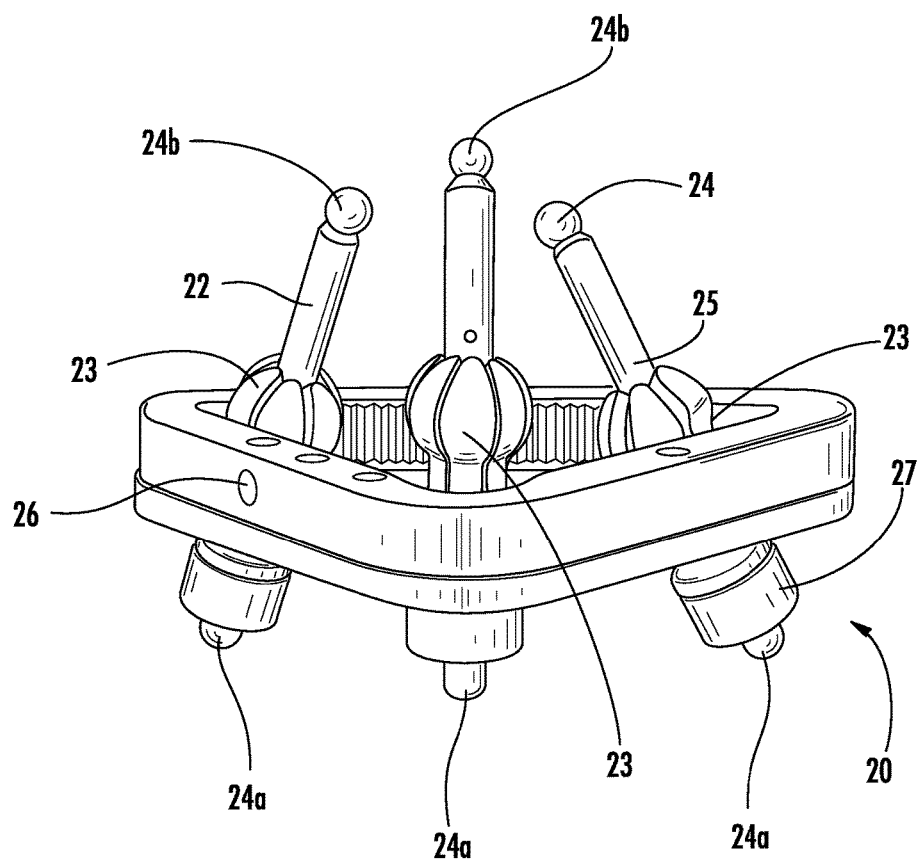
FIG. 1 is a perspective view of the first main frame (the second is the preferred embodiment) with a thin, top plate-like surface removed to expose, for illustration purposes, the interior spherical surfaces which provide the spring-biased, outwardly, telescopic columns with rotational flexibility (6 degrees)

Description will now be given of the invention with reference to the attached FIGS. 1-23. It should be understood that these figures are exemplary in nature and in no way serve to limit the scope of the invention as the invention will be defined by the claims, as interpreted by the Courts in an issued US patent.

The present invention discloses the individual components, system, and method for preparing a set of dentures, preferably in a single visit, by using the patient's own mouth as the articulator for preparation and creating the end-product, a set of dentures for a patient. To prepare a set of dentures according to the present invention, the dentist will first take or create an impression of the patient's lower jaw or mouth and upper jaw or mouth. Typically, these patients are edentulous so that the dental impression obtained from the inventive trays disclosed herein show no teeth but, rather, provide a negative of the internal gums and anatomical structure of the mouth, but basically, the gum lines. Of course, the present invention can be used where one or more teeth are present in the mouth of the patient and, in addition, the present invention can be used for other dental procedures, not requiring a complete set of dentures at all, but where a single tooth is required, a bridge, a partial denture, an implant, etc. Basically, the present invention is a simple and complete mechanism for using the patient's own mouth as the articulator for producing a positive image of the patient's existing mouth and orienting teeth with respect thereto for providing an attractive set of teeth.

The impressions are taken of the upper and lower gum configurations by means of an upper and a lower tray which is first filled with dental impression material. When placed in the mouth of a patient, the impression material will mold around the gums and configuration of the mouth and harden or cure to form a negative of the patient's upper or lower gum structure.

Lower tray 30 (See FIGS. 11 a-g) comprises a trough similar to a typical lower jaw or lower tooth dental tray (curved to hold impression material and with upper rear and forward edges to hold the material therein during formation of the impression) and, in addition, comprises a set of radially and inwardly extending platforms 32, preferably three are provided, having small, magnetic holding areas 33 at or near the ends of the platforms 32. These platforms 32 are co-planar and define supporting areas for the main frame 20 or alternative and preferred, main frame 50 (both described hereinafter) and specifically the location nubs 24 or small balls 56 of columns 22 and telescopic screws 52, respectively (See FIG. 4 for main frame 20 located on platforms 32 of the lower tray 30 and FIG. 14b for illustration of the main frame 50 supported on platforms 32 of the lower tray 30). A small ridge element 35 extends forwardly of the front edge of the lower tray 30 and cooperates with a handle 34 for allowing the handle to be snapped on and held to the lower tray 30 and, easily, removed therefrom, as desired. For use of the lower tray in creating an impression of the lower gums, the handle 34 is placed on the lower tray by first tilting the handle 34 so its rear and separated hooks 37 grip a small flange 39 of the lower tray. Small flange 39 extends to both sides of the front platform 32 (see FIG. 11c) and its thickness is substantially the same as that of the dimension between the bottom of the front of the handle 41 and the top of the hooks 37. In this manner, the hooks 37 are gripped over the flange 39 and then the front set of hooks 43 snap over and beneath the front ridge 35 of the lower tray 30. The front hooks 43 can be provided with small nubs to hold the handle 34 to the lower tray 30 until desirably removed. Towards this end, the front hooks 43 are somewhat resilient to allow them to flex toward the proximal end 45 as the handle is lowered and snapped over the flange 39 and the front ridge 35, and, then, when the nubs clear the bottom of the front ridge 35, the resiliency of the front hooks snaps rearwardly to hold the handle 34 to the lower tray 30. Removal of the handle 34 is easy and quick, basically pivoting the proximal end 45 while holding the lower tray 30. This will allow the front hooks 43 and their small nubs to disengage from below the front ridge 35 and, once they clear by further pivoting the rear hooks 37 can be easily removed from the small flange 39 of the front platform 32 of lower tray 30. The handle's rear hooks 37 are spaced (See FIGS. 11b and 11c) so that they grip over the small flange 39 of the platform 32 but do not cover the magnetic button 31, rather, the hooks 37 grip over and secure to the platform 32, on the outside of the centrally located magnetic holding area 33 with a button-like magnetic element 31.

Lower tray 30 is provided with a removable and snap-on/snap-off handle 34 which is preferably made of plastic. It is used for creating a first dental impression, a negative, of the patient's lower jaw or mouth/gums. The platforms 32, with magnetic holding areas 33 will support the telescopic columns 22 of main frame 20 or the telescopic screws 52 of the preferred main frame, so-called main frame II, depicted in the Figures as element 50. The platforms of the lower tray 30 and, specifically the magnetic holding areas are provided with small button-like magnetic elements 31 for releasably yet significantly holding the location nubs 24 or round metallic balls 56 of the telescopic columns 22 or the telescopic screws 52 of main frame I (element 20) or main frame II (element 50), respectively.

An upper full tray (not shown) can be used with the present invention for forming an impression of the patient's upper jaw or mouth/gums. This upper tray can be conventional, i.e., is readily available from commercial sellers. Alternatively, an upper tray 61 can be provided, substantially identical to the lower tray 30 but sized and shaped to accommodate the roof of the mouth. It, too, can be provided with platforms, magnetic holding areas and a snap on/snap off handle. It is used to create a dental impression of the patient's upper mouth or gums for use in connection with formation of dentures.

According to another embodiment of the present invention, a palatal tray or palatal contact piece is provided. It roughly corresponds to the patient's roof of the mouth only, i.e., it is not intended to conform to the patient's upper gum ridge. This palatal tray 40 (see FIGS. 4, 5, 12a-1, 13a, and 14b-d and f-j) is similar to the lower tray 30, and is preferable formed of plastic, too. It has a convex-shaped hill or roof section 51, a rear edge 53 and two side edges 55. The roof section 51, when viewed from above, defines a basic isosceles triangle with curved corners. Near each of the corners, a button-like magnetic element 31 is provided which is held in the plastic so as not to be removable therefrom but which are exposed through the bottom 59 of the palatal tray 40. The top 57 of the palatal tray corresponds to the top surface of the roof section 51 and will lie directly in contact with the patient's roof of their mouth, when the palatal tray 40 is inserted therein, held on top of the main frame I (element 20) or preferably, on main frame II (element 50). The button-like magnetic elements 31 of the palatal tray 40 will capture and hold, releasably, the location nubs 24 or small balls 56 at the tops of the telescopic columns 22 or telescopic screws 52 of the main frame I (20) or main frame II (50), respectively, as seen in FIGS. 4 and 5, and 14 *a-d* and 14 *f-j*, respectively.

Figure 2:
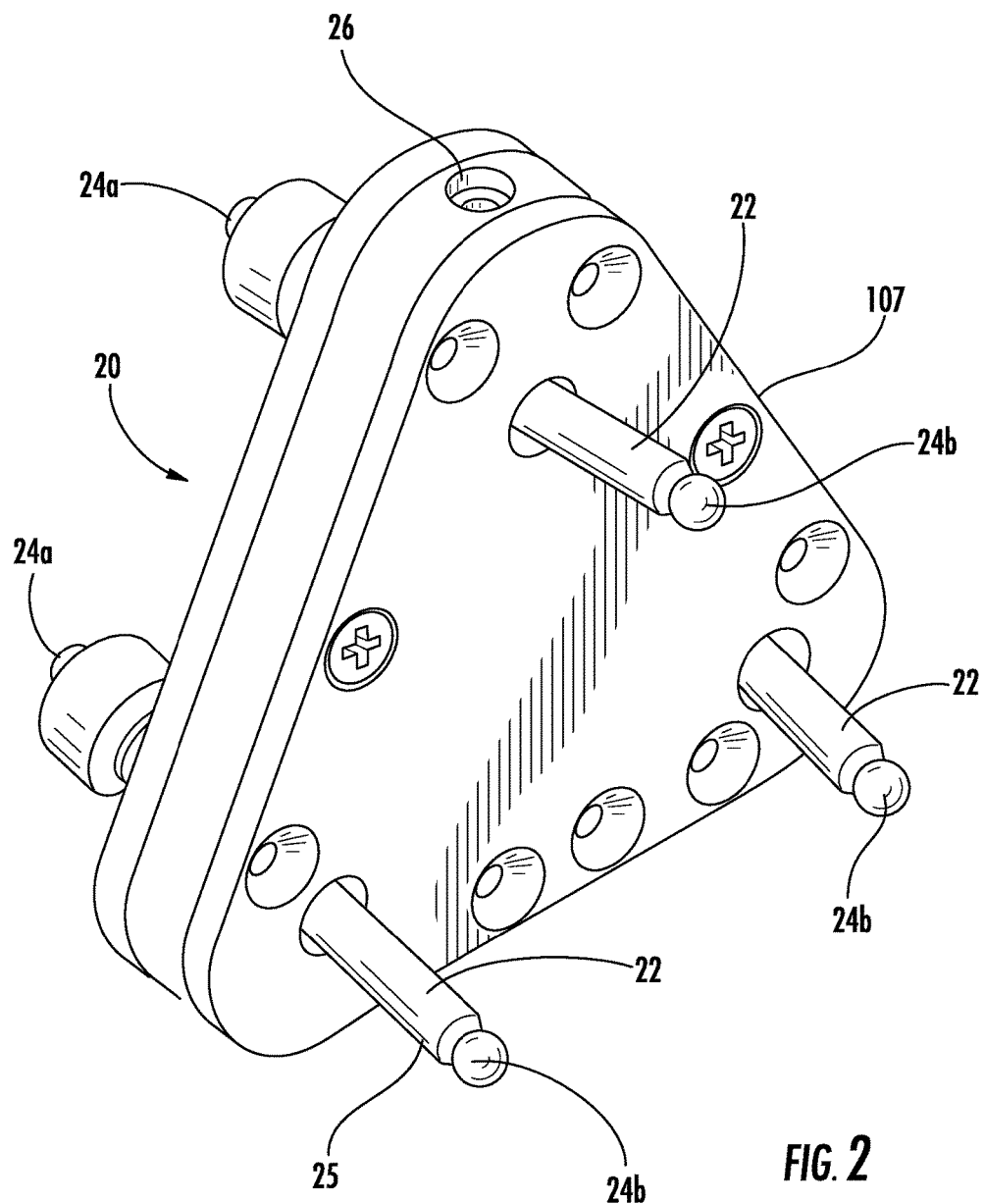
FIG. 2 is an top perspective of the first main frame depicted in FIG. 1 but with the spherical surfaces contained therein as the top plate-like surface has been secured and showing the ends of the metallic telescopic columns and also showing one locking mechanism (set screw) at a vertex of the main frame for securing the columns at desired heights and relative angular position.
Figure 3:
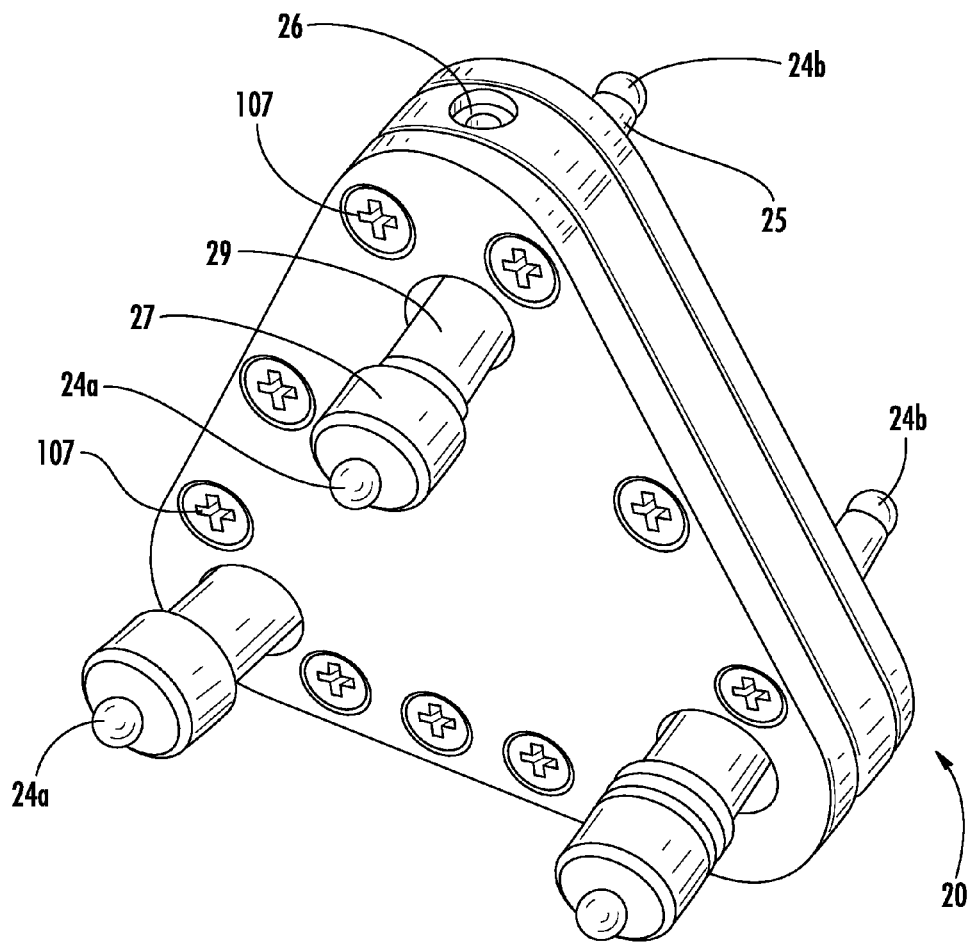
FIG. 3 is a bottom perspective view of the first main frame shown in FIG. 1.

Main Frame I, element 20, is shown in FIGS. 1-3. It comprises and defines a basic triangular shaped plane 100 formed of three layers of metal, 101, the top layer, 103, a bottom layer and a hollow triangular middle layer 105. Together they form a triangular sandwich with curved corners. The hollow and middle layer 105 contains small mechanical and moving components to allow the device to lock the telescopic columns 22 in relative location. Set screws 26 are approachable through bores 27 located at the front (see FIG. 2), or either side (see FIG. 1) of the main frame 20. Also, a set screw 29 can be provided in the rear of the middle layer 105. The set screws 69 and 29 will mechanically cause a set of internal mechanical components (described below) to cooperate which will cause pressure to be applied to the three telescopic columns 22 to hold the same in place, as desired, after adjustment.

The top layer 101, bottom layer 103 and middle layer 105 of the triangular plane 100 of main frame I (element 20) are held together by several screws 107 which pass through bottom layer 103 and into and captured by screw threads of middle layer 105, and additional screws 107 pass through top layer 101 and are captured by screw threads of middle layer 105. The three telescopic columns 22 are shown with their ball or spherical surfaces 23 exposed in FIG. 1, but shown fully enclosed by the top, middle and bottom layers, 101, 105, and 103, respectively, in FIGS. 2, 3, and 4. The columns 22 comprise small diameter, upper cylindrical rods 25 which have at their distal ends, small location nubs 24, also referred to as 24*b* (see FIG. 1). These location nubs are preferably made of magnetic or ferro-magnetic material so that they will be attracted to and held, until deliberately dislodged by the dentist, to the button like magnetic elements 31 of platforms 32 of the upper or palatal tray 40. The bottoms of the telescopic columns 22 are formed of location nubs 24, (also referred to as 24*a* in FIG. 1) which will also be of magnetic or ferro-magnetic material to be attracted to and held, until deliberately dislodged by the dentist, to the button like magnetic elements 31 of platforms 32 of the lower impression tray 30. Each lower column is threaded above the location nubs 24 or 24*a* and a small disc 27 formed and screwed onto the threads. Proceeding upwardly from the location nubs 24 or 24*a*, the lower rod segment of the columns 22 are of a diameter slightly larger than the diameter of the upper portions of the rods 25. Thus, the upper portions 29 of the lower rod segments fit over and allow the upper rods 25 to slide within the same. A spring (not shown) is within the telescopic rods 25 and 29 and the bias of the spring serves to expand the distance between the location nubs 24*a* and 24*b*, unless the force of the spring is overcome by movement of the patient's mouth when the main frame is located within the same and a "bite" is accomplished. This causes the springs to individually compress which causes the smaller diameter upper rods 25 to slide within the relatively larger diameter lower rods 29. The uppermost section of the lower rods is provided with a split, bulbous, collar or spherical surface 23, which surrounds the upper rod 25. The spherical surfaces 23 are maintained within the main frame 20 and, yet, allow for the telescopic columns 22 to have substantial degrees of movement within the main frame 20, until the entire device is "locked down." Thus, each telescopic column is able to move about the pivot point defined by the spherical surfaces within the triangular plane 100 of main frame 20, so that the upper location nubs 24*b* can move front to back, side to side and in positions, therebetween, as the lower location nubs 24*a* move in the relative opposite direction. And, while capable of moving about the spherical surfaces 23, each telescopic column is also capable of decreasing and increasing its relative distance between upper location nubs 24*b* and lower location nubs 24*a*, while supporting the palatal tray 40 (nubs 24*b* sit in and are attracted to button like magnetic elements 31) and supported by the button like magnetic elements 31 of lower tray 30, on the platforms 32), respectively. The relative flexibility, vertical extension and contraction, and degrees of movement of the palatal tray, lower tray and the main frame are clearly shown in FIGS. 12*f* through 12*l*.

Figure 4:
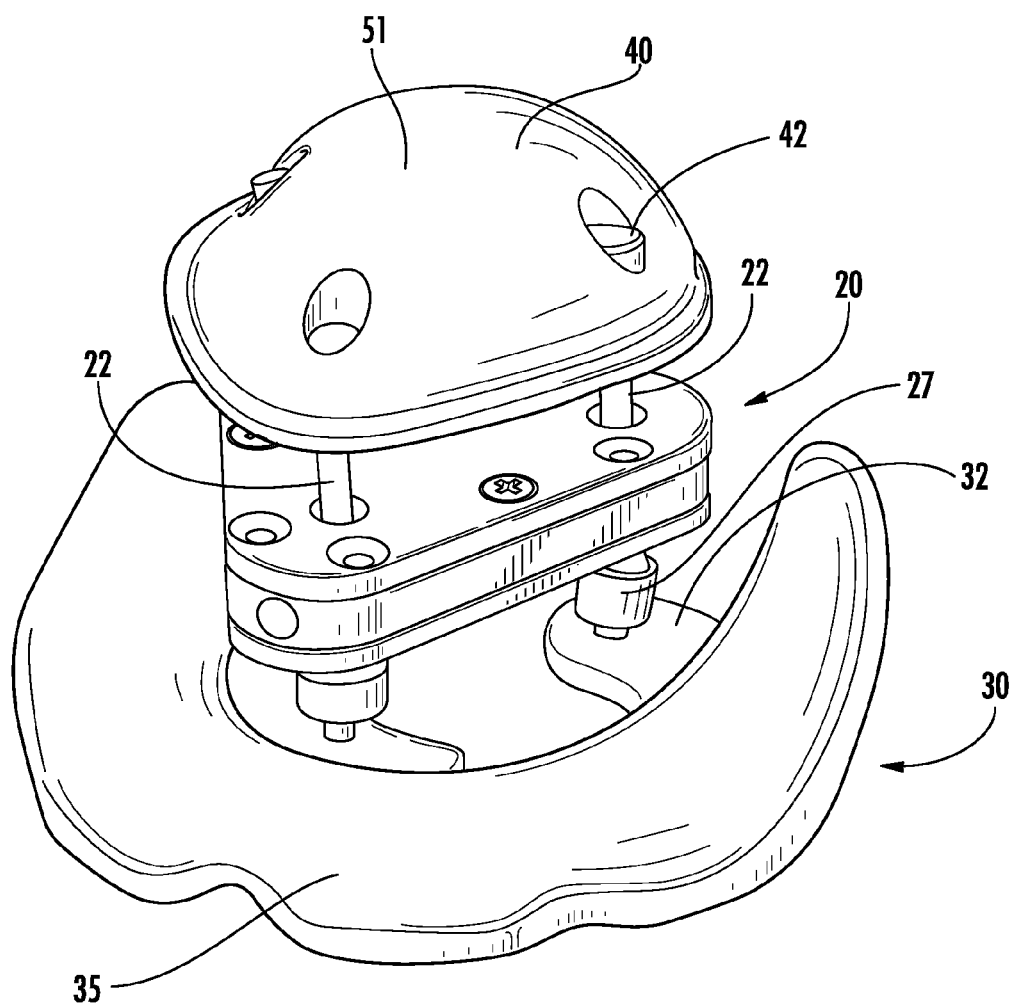
FIG. 4 is a side perspective view of the first main frame supported on the inventive lower impression tray and also having, supported on the upper ends of the telescopic columns, an upper palatal tray—each tray is magnetically secured to the top and bottom ends of the columns, respectively, by having the platforms of the palatal tray sit on the top ends of the columns and the bottom ends of the columns sitting upon the platforms of the lower impression tray.
Figure 5:
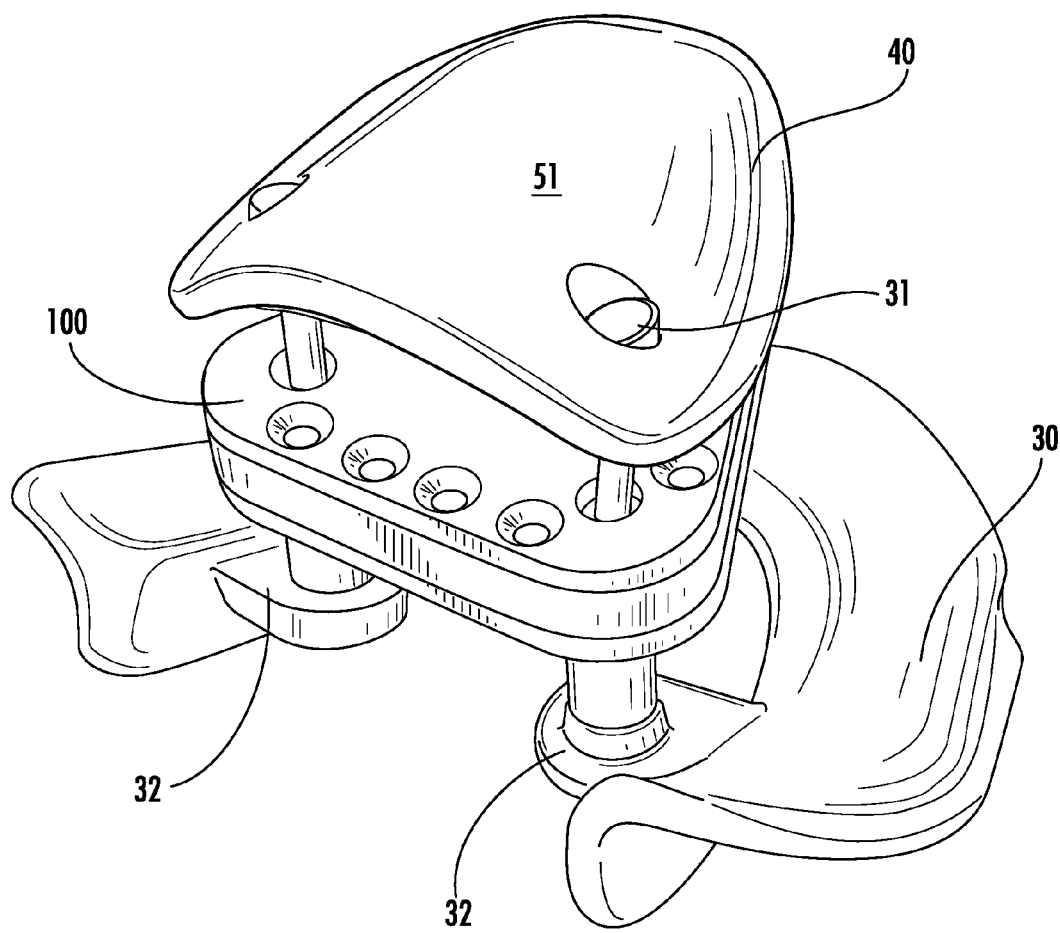
FIG. 5 is a rear perspective view of the first main frame with lower impression tray and upper palatal tray shown in FIG. 4. The platforms for the trays magnetically locate and secure the lower tray and the palatal tray to the columns of the main frame.

FIGS. 4 and 5 illustrate the location of the main frame I (element 20) on the platforms 32 of the lower tray 30, by the lower location nubs 24*a* sitting on the button like magnetic elements 31, and the palatal tray 40, supported by the upper location nubs 24*b*, at the ends of the upper rods 25, fitting within and magnetically attracting the button like magnetic elements 31 of the palatal tray. It will be appreciated that there is spatial locational flexibility to the location of the palatal tray 40 with respect to the lower tray 30, with the main frame 20, located therebetween. When the device comprised of main frame, upper or palatal tray, and lower tray are located within a patient's mouth, and the patient is told to "close" or "bite gently," the relative vertical spacing, locations of the palatal tray and the lower tray will assume an orientation and spacing corresponding to that of the patient. Then, using a small Allen wrench or other tool, the lips of the patient can be spread and the tool inserted, from the front to the front set screw or from the side to the side set screw, to lock the positions of the telescopic columns, the palatal tray and the lower tray with respect to one another and to the main frame. This is an important and significant step in the making of the dentures, using the components disclosed herein and the process described herein.

FIGS. 12*b* through 12*d* show the middle layer of the main frame 20 and its mechanisms for locking the spherical surfaces 23 of the telescopic columns 22. Viewing FIGS. 12*d* and 12*e*, the middle layer 105 of the main frame 20, contains a front plate 201, a rear plate 203, a pair of side plates 205 and a pressure plate 207. They cooperate together, with movable and sliding surfaces along one another to allow (when the set screws 26 are untightened) motion and adjustment of the telescopic columns 22, as described above, and their spherical surfaces and, when the set screw(s) are tightened, to lock the orientation and spacing of the columns in place. All plates, front plate 201, rear plate 203, side plates 205 and front pressure plate 207, are provided with flat top and bottom surfaces which lie between and are capable of moving between the top layer 101 and the bottom layer 103. The plates, 201, 203, 205 and 207 are slidable on the inside surfaces of top and bottom layers 101 and 103, and are confined within the interior side walls of the hollowed out middle layer 105. At the front of the middle layer 105 is a front pressure plate 207. The front pressure plate 207 is wider than the bore for the front set screw 26 but the set screw bears directly upon one side thereof. The rear surface of the front pressure plate is curved and in contact with the front surface of the spherical surface of the forward-most column 22. Behind that column 22 is the front plate. It has a front contact surface, rounded as is the rear of the front pressure plate 207, which bears against the rear surface of the spherical surface of the forward-most column 22. The front plate has a pair of outwardly divergent sides 208 and 209, which slide against the inside wall 210 of the middle layer 105. The front plate 201 has a rearwardly protruding tail member 211, which extends along and is aligned with the center axis of the bore of the set screw and the rear set screw and its bore (see FIG. 12d). The rear of the front plate 201 has two flat surfaces 213 and 215 with the protruding tail member 211 therebetween.

The side plates 205 are each provided with curved surfaces 220 which bear against the spherical surfaces 23 of the telescopic columns 22. They each have side surfaces 217 and 219 which slide along the inside wall 210 of the middle layer 105. A rear surface 221 is provided, too.

The rear plate 203 is an A-shaped element (see FIG. 12e). It has front surfaces which bear against the rear sides 213, 215 of the front plate 201, a set of small mitered side walls which bear against and slide along the inside wall of the middle layer 105, rearwardly angled set of walls 231, which bear against and slide over sides 217, 219 of side plates 205, and a small rear wall 240, which has the bore for the rear set screw therein.

In use and operation, when the set screws 26 in the front and the rear of the middle layer 105 are untightened, the plates within the middle layer 105 slide between top and bottom layers 101 and 103, so that the telescopic columns and the spherical surfaces thereof can be adjusted, so that the location nubs 24a and 24b can move, on the platforms of the lower tray and the palatal tray, 30 and 40, respectively, so that the palatal tray is comfortably and properly located within the patient's mouth and the lower tray, too, properly and comfortably located, all with the main frame therebetween. The plates move with respect to one another so that front, rear, side and pressure plates, 201, 203, 205, and 207, slide and shift, within the inside wall of the middle layer to accommodate the movement of the spherical surfaces 23 between the curved surface of the pressure plate 207 and the curved surface of the front plate 201, and between the curved corner of the inside wall of the middle layer 105 and the curved surfaces 220 of the side plates 205. Tightening of the set screws, 26, front and rear, causes the rear of the set screw in the front to bear against the front of the pressure plate 207 which is pushed forwardly by the rear plate 203, moved forwardly by the rear set screw, by its interaction and sliding movement of rear plate 203. And, as the rear plate 203 is moved and shifted forwardly, by the rear set screw being tightened and bearing against the rear surface of the rear plate, the side plates are forced towards the spherical surfaces of the rear telescopic columns so that they, too, are squeezed and held in place, preventing further rotation, holding the spherical surfaces between the curved surfaces 220 of the side plates 205 and the inside curves of the middle layer, at the rear corners.

Tightening of the set screws causes the plates to shift and to secure the columns in place and in orientation. It also causes the squeezing and securement of the split neck, collet 31 about a bulb element of the inside upper rods 25 to secure the height of the columns, i.e., the distance between location nubs 24a and 24b are secured, as required.

An alternative and preferred embodiment of the main frame 20 is shown as main frame II, element 50. This device is best seen in FIGS. 6, 7, 14a-j and 15a-e.

Main frame II or the preferred embodiment of a main frame, is preferably made of metal and has a horse-shoe general shape, two legs 51 and 53 connected by a central arch 55. A top surface 57 and a bottom surface 59 are defined. The top and the bottom surfaces, 57 and 59, are separated from one another at the front of the device by a horizontal slit 61. Three telescopic screw members 56 pass through the main frame 50, one at the central arch 55, one each at the rear of the legs 51 and 53. These are functionally similar to the telescopic columns used in main frame I, element 20. The screw members 56 have locating nubs 56 at their ends, the nubs being magnetic or ferromagnetic and attractively held or secured to the button-like magnetic elements 31 of the supporting platforms 32 of the lower tray 30 and, on the top of the telescopic screw members 52, the locating nubs attractively and magnetically hold the palatal tray thereto. The telescopic screws pass through the main frame 50 and the exterior screw threads of the screw members 52 engage with internal screw threads of the top and/or bottom 57 and 59 of the main frame 50. Rotation of the bottom of screw member 52 will cause the bottom locating nub 56 to move toward and away from the bottom 59 of the main frame 50. The bottom segment of the screw members 52 can be provided with turning wheels or knurled sections to facilitate the rotation of the bottom members of the screw members with respect to the bottom and top of the main frame II, element 50. The telescopic screw members, on their top segments, are provided with screw threads which project into internal screw threads of the top of the main frame 50 and also allow the telescopic upper section to thread into the bottom section. A turning wheel or knurled section is located about the top section, too, to facilitate rotation of the same into the main frame, out of the same, and into and out of the corresponding telescopic member of the same screw member 52. A locking nut also surrounds the bottom screw segment to secure the expansion or contraction of the telescopic segments of the screw members 52, when their spacing and extension/contraction is desirably set.

Figure 6:
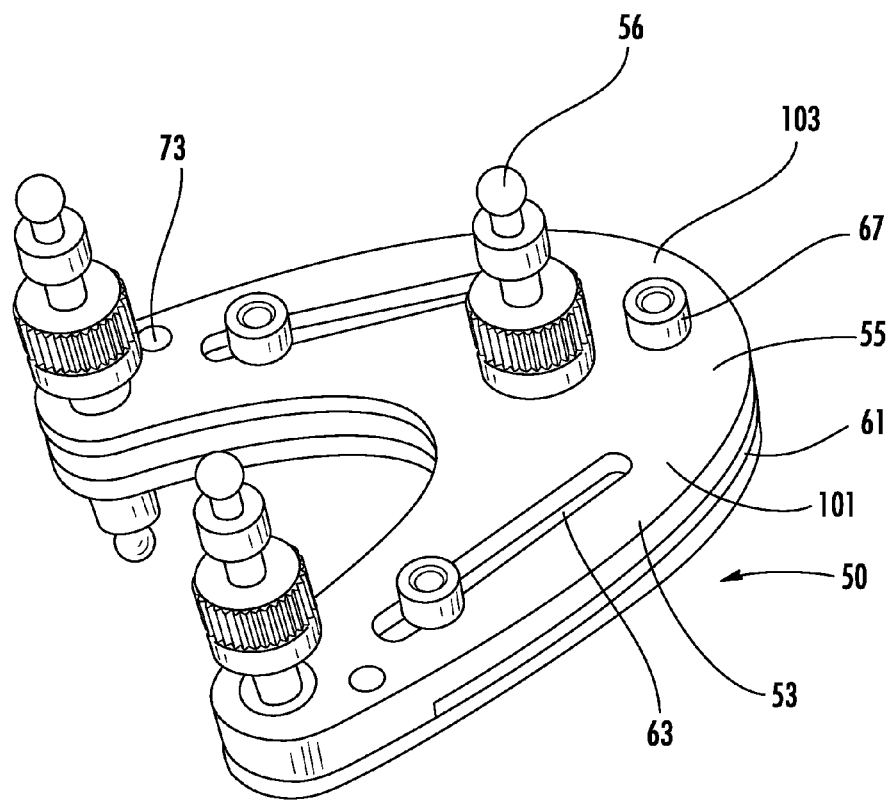
FIG. 6 is a rear perspective view of the second and preferred embodiment of the main frame for use with the present invention, as a substitute for the main frame of FIGS. 1-5. This main frame is shown removed from an upper and lower impression tray. This main frame shows columns or telescopic screws passing through the plate of the main frame and protruding through both sides of the main frame, each end of each column being provided with a magnetic connector or ball-like end to magnetically attach to the inwardly projecting magnetic platforms of the upper and lower impression trays, each column being provided with two telescopic screw segments to help extend or contract one telescopic screw within the other to adjust the same about the surface of the plane defined by the top of the main frame and a locking nut to hold the relative telescopic screw segments in position.

A pair of slots 61 are provided on both sides of the central arch, within the leg 51 and 53, the slots 61 passing through the top and bottom 57 and 59, respectively, of the main frame II, element 50. The central arch 55 is provided with a pair of aligned holes 71 which also pass through the top and bottom 57 and 59, respectively, of the main frame II, element 50. A small plate 69 (see FIG. 9) is provided with a threaded opening and it receives a holding screw 67 (See FIG. 6). Similarly, plates 65 are provided on the bottom 59 of the main frame II, element 50, and connected and held there by holding screws 67 which are directed into and captured by threaded openings in the plates 65. Those holding screws 67, when tightened by slit 61, will cause the split in main frame 50 to have the bottom approach and near to the top, squeezing together and thus holding the occlusive plane and the units or sets of teeth (to be described hereinafter) onto the main frame. The plates 65 and the holding screws 67, passing through the slots 63, allow the clamping of the fork-like holding members of the occlusal plane and the units of teeth, to be shifted into position. Stated differently, the holding screws and the plates can slide along the slots 63 and once positioned (with the fork of the teeth held therein) the holding screws tightened to compress the top 57 to the bottom 59, to squeeze and hold the forks of the units of teeth in place. The front plate 65 and its holding screw are provided to hold and secure (and allow selective removal) of the occlusal plane and the front set of teeth. According to the present mode of making the present invention, the top and bottom, 57 and 59, of the main frame II (or element 50) are formed from thin sheet metal and then secured together via back screws 73 (see FIG. 9) which are captured by internal screw threads in the top 57 of the main frame II, element 50. Suitable spacer elements 75 are provided between the rear of the main frame II's top and bottom sections, so as to define the horizontal slit 61, extending from just in front of one of the rear telescopic screw members 52 to the front central arch 55 and around to the other rear telescopic screw member 52 (as seen in FIG. 6).

An occlusal plane 70 is provided for facilitating the dentist's procedure. This device is a thin sheet of metal, in an arc shape, which is intended to surround the outside of the patient's mouth and face. FIGS. 15a, 15b, and 15c, illustrate the same. The occlusal plane 70 has an interior arc 77 and an exterior arc 79, defining a band 81 therebetween of substantially constant width. Extending rearwardly from the interior arc 77 of the occlusal plane 70 is a thin metal fork 72. The fork 72 has a pair of adjacent and parallel tines, separated by a small space. The fork 72 can slide between the top 57 and bottom 59, i.e., within the horizontal slit 61. The occlusal plane can be used to ensure that the horizontal slit 61 and the teeth of the patient are consistent with dental principles, taking into account the patient's anatomy, including, for example, the eyes, nose, ear tips, etc., including also the ala tragus. The large arc in the form of the occlusal plane 70, secured, even temporarily, to the front of the main frame (element 50) by the fork 72 sliding into the horizontal slit 61, with the tines of the fork extending on both sides of the holding screw at the central arch 55 facilitates this effort. The telescopic columns 22 and the telescopic screws 52 can be adjusted within the patient's mouth, while the dentist uses the occlusal plane 70 as a plane of reference. Once the adjustments are made, the occlusal plane is removed and the locking or knurled locking knobs tightened down so that accidental change of positioning cannot be done.

Artificial teeth, set in two types of wax, are provided, in accordance with the present invention. These can be understood by review of FIGS. 8, 9, 10, 16a-d, and 17a-e). The artificial teeth are preferably acrylic and preferably will be the actual teeth provided to the patient by the present invention, a set of teeth, preferably in a set of complete acrylic dentures. The teeth are provided in one or two waxes, the function of which will be described. A set of teeth is preferably a partial set of uppers and corresponding lowers. The teeth will be provided to the dentist and he will select the sets which most properly correspond to the type of teeth to be fitted, the color and size, too. So, a dental office may have many sets of available teeth. According to the present invention, a front integrated set of six upper and six lower teeth are provided; a set of four right upper and four right lower teeth are provided, and a set of four left upper and four left lower teeth are also provided. This will provide, if required, a complete set of new dentures to the patient, comprising 14 upper teeth and 14 lower teeth. Each set of acrylic teeth is provided with a wax-like gum to hold adjacent and opposed (upper opposed to lower) teeth of the sets of teeth or a unit of teeth. Each set of teeth is provided with a connector or a fork 66, similar to the connector or fork 72 of the occlusal plane 70. The fork allows front teeth (six lower and six matching upper) 64 to be secured onto the main frame II, element 50, by having the tines of the fork 66 slid into the horizontal slit 61 and held around the front holding screw 67. Left side teeth 60 (four upper and four lower) and right side teeth 62 (four upper and four lower) are also provided with a rearwardly extending fork 66 with separator tines for securing to main frame II, element 50. The fork is provided with a front pair of upwardly turned and extending flanges 83 (see FIGS. 16a and 16c) and a single, central located downwardly turned and extending flange 85. The flanges are located within and covered in wax so that the forks 66, with the flanges and wax, fully support the teeth, when the same are inserted into the horizontal slit 61 of the main frame II, element 50. The front teeth are inserted into the front of the main frame II, element 50, by having the tines on both sides of the holding screw at the front of the central arch; the left side teeth 60, inserted into the main frame II, element 50 (with tines of fork 66 passing into the horizontal slit 61 and the tines extending around the holding screw 67); and the right side teeth 62 inserted onto the main frame II, element 50 on the relative right side of the frame for the patient, with the tines of the fork 66 extending around the holding screw 67. The complete set of acrylic teeth, front 64, right side 62 and left side 60 are held on the main frame II, and, then, the holding screws tightened to hold the same in place. If necessary, the front, left side teeth and right side teeth 64, 60 and 62, respectively, can be placed in warm water or run under warm water so that the wax becomes malleable. This will allow the dentist to more properly conform the curvature of the arches of the teeth units to the patient's actual arch and gum line.

The teeth units or sets, 60, 62, and 64, when properly shaped and placed into the slit 61 of main frame II, element 50, can be installed into the patients mouth, supported by the telescopic screws 52 on the supporting platforms 32 (more exactly, upon the magnetic holding areas), with the palatal tray 40 and its magnetic holding areas superimposed, too, on the location balls 56 of the upper portions of the rods of the telescopic screws 52. Once the dentist and patient are comfortable with the fit and the aesthetic look of the teeth, the holding screws 67 are tightened. As mentioned, the holding screws and side plates 65 are slidably movable along the length of the slots 63 and in this manner, the side (left and right) sets of teeth can be precisely adjusted, forwardly and rearwardly, in and out. Once the holding screws are tightened, after the telescopic screws have been fixed in position, the entire device, lower tray 30, upper or palatal tray 40 and main frame II, element 50, with attached sets of teeth, 60, 62, and 64 are removed from the patient. The patient's mouth has, in effect, with the components disclosed and described herein, served as the articulator. Now, what remains is converting the location, orientation, and placement of the actual acrylic teeth, sets 60, 62 and 64, into hard acrylic upper teeth dentures and lower teeth dentures.

Figure 18:
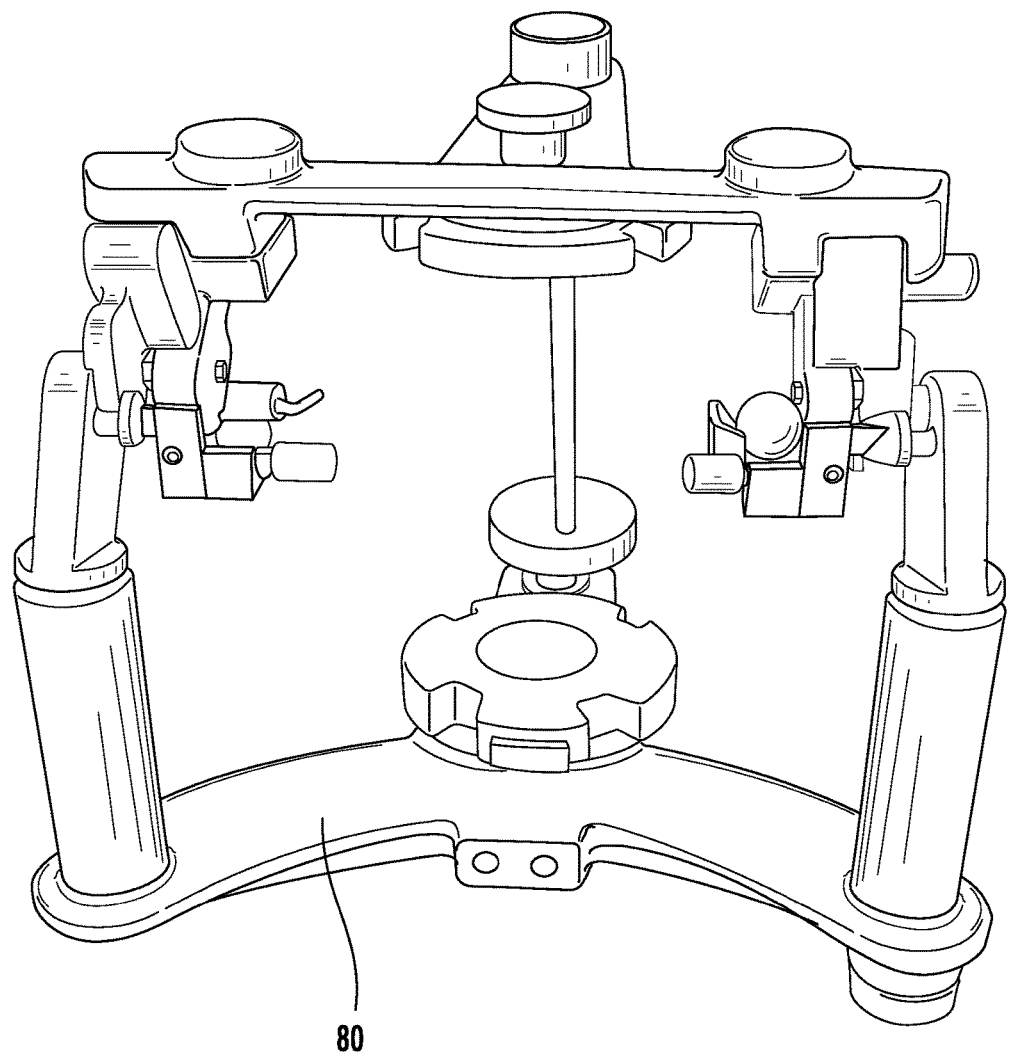
FIG. 18 is a rear perspective view of a standard or commercially available dental articulator, intended to be used with the present invention, to hold the stone models of the patient's mouth in place for proper positioning.
Figure 19:
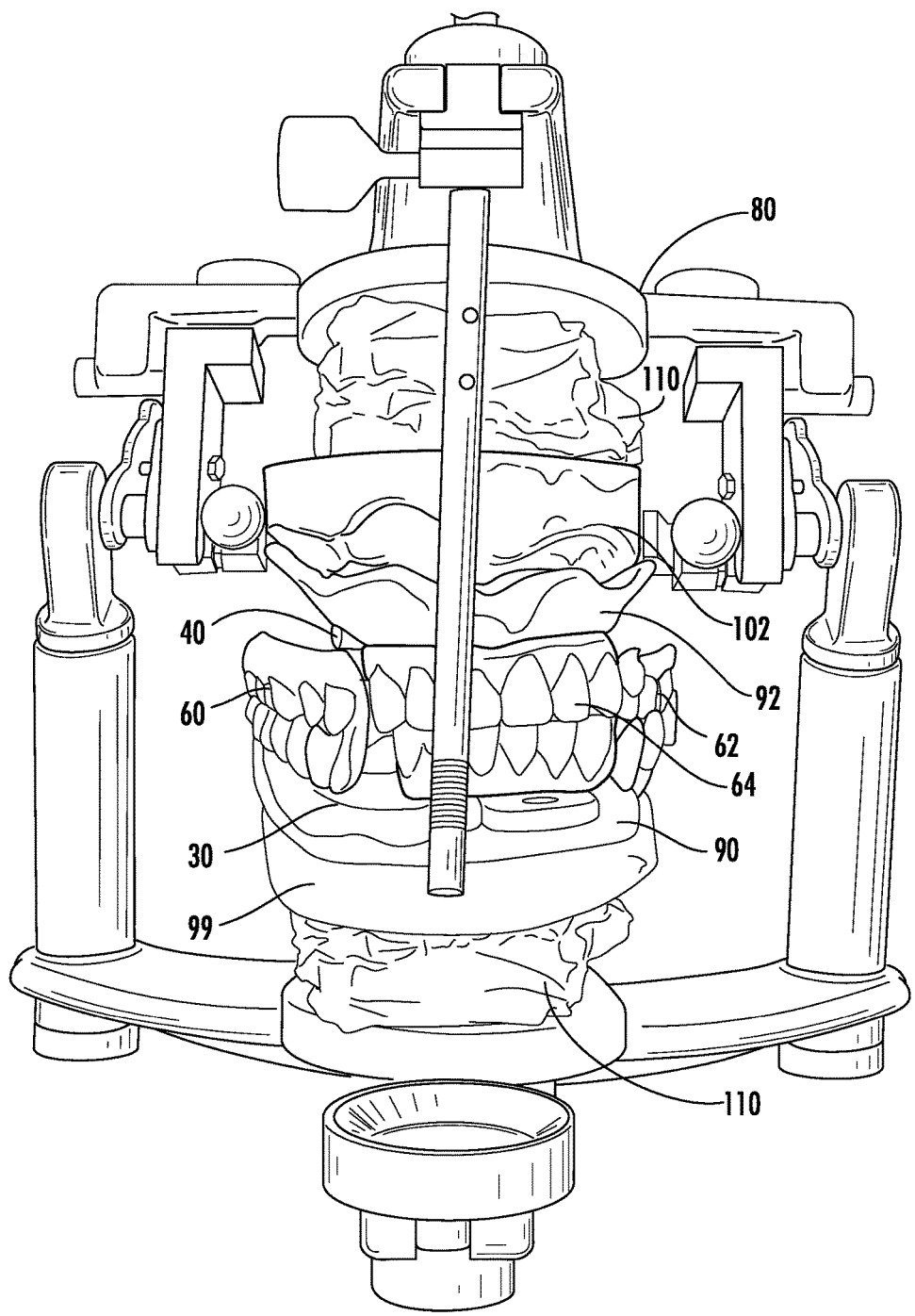
FIG. 19 is a front, perspective view of the "dental sandwich" formed by the top and bottom stone models, the custom trays, and the palatal tray, the lower impression tray and the main frame, element 50, with sets of front and side teeth, held in the main frame, in a dental articulator with dental plaster on the top and bottom and before base wax is used for the connection between the custom trays and the wax holding the teeth together.

According to the preferred embodiment of the present invention, a conventional and commercially available articulator 80 is used. This is shown in FIGS. 18 and 19 and other, similar mechanical articulators can be used for the same general purposes and steps of transferring the waxed-together teeth on the main frame into a set of upper and lower dentures.

Figure 20:
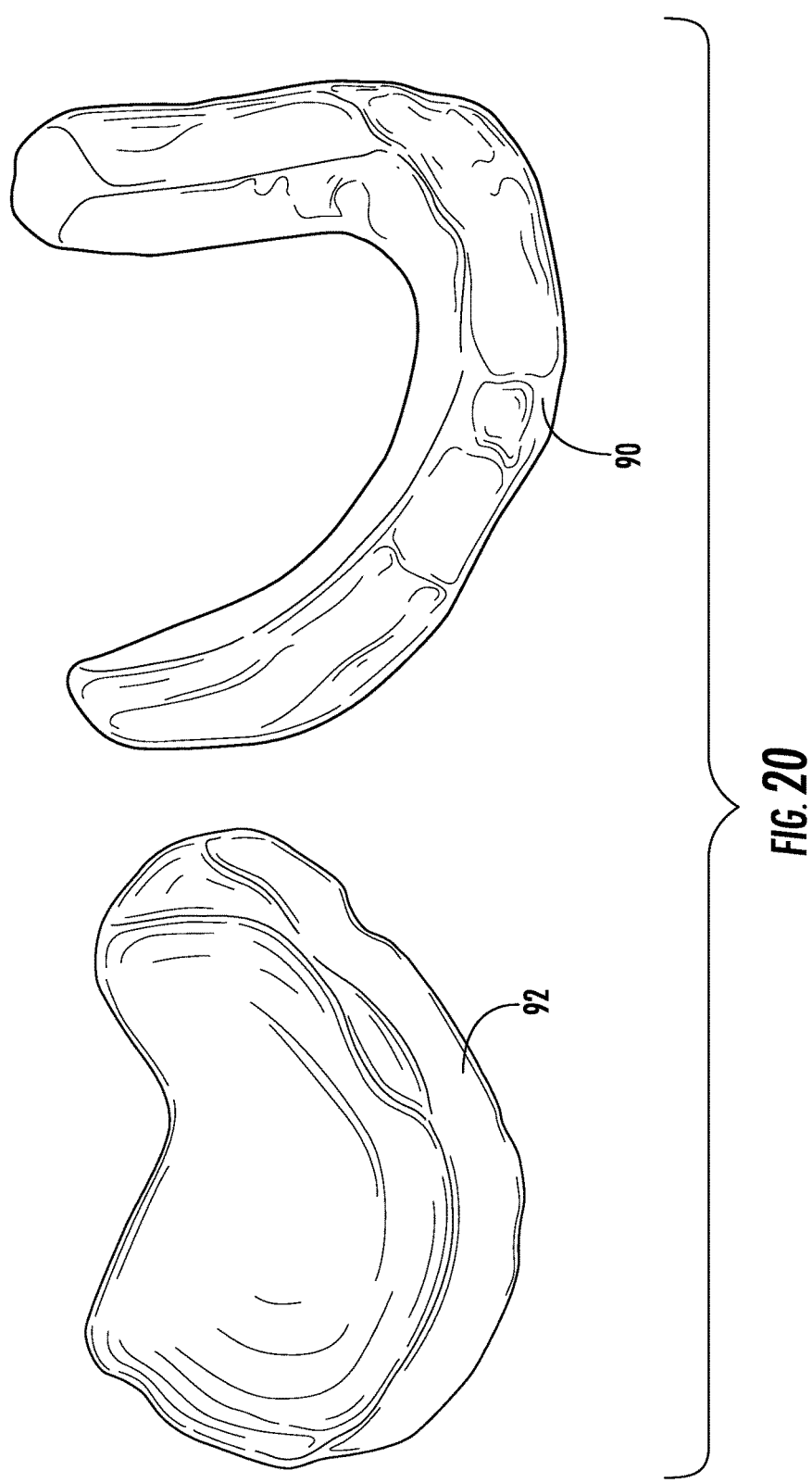
FIG. 20 is a top, front and side perspective view and the bottom, front and side perspective view of the custom trays formed of the lower and upper mouth, respectively.

FIG. 20 shows the custom trays formed by the use of an upper tray 61 and a lower tray 30 which are used to form negative impressions and then stone models. From here, custom trays are made. These are shown in FIG. 20 as lower gum ridge negative impression 90 and upper roof impression 92. These were made by use of lower tray 30 and upper tray 61, a conventional such tray and/or by a customized tray similar to that used for the lower impression. FIG. 21 shows the other or flip sides of the custom trays 90 and 92. The sides shown here actually are the "contact" sides with the patient's roof of the mouth (custom tray 92) and the gum ridge, custom tray 90.

Figure 22:
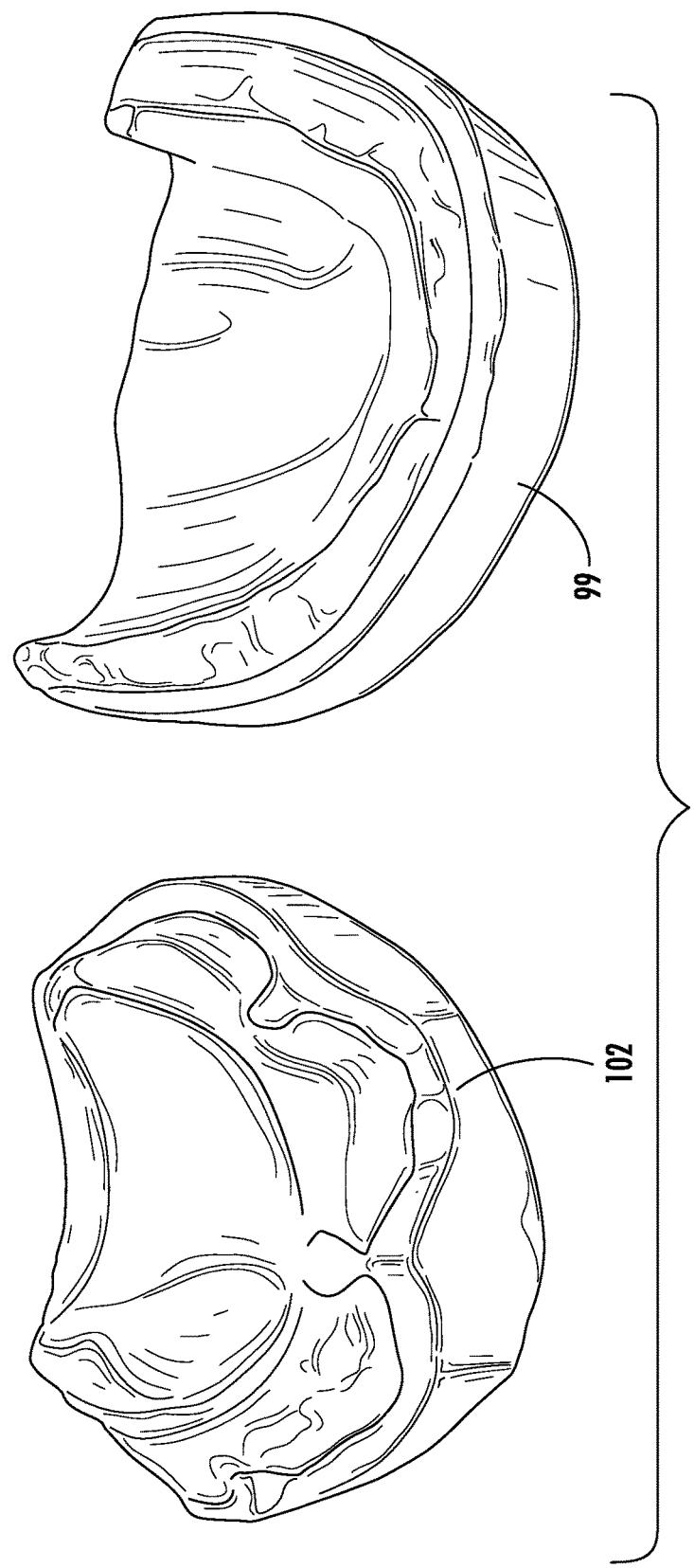
FIG. 22 is a front and top perspective view of stone models formed consistent with the present invention, of the upper and lower mouth of a patient, created by pouring dental stone onto the impressions formed by the dental trays of the present invention.
Figure 23:
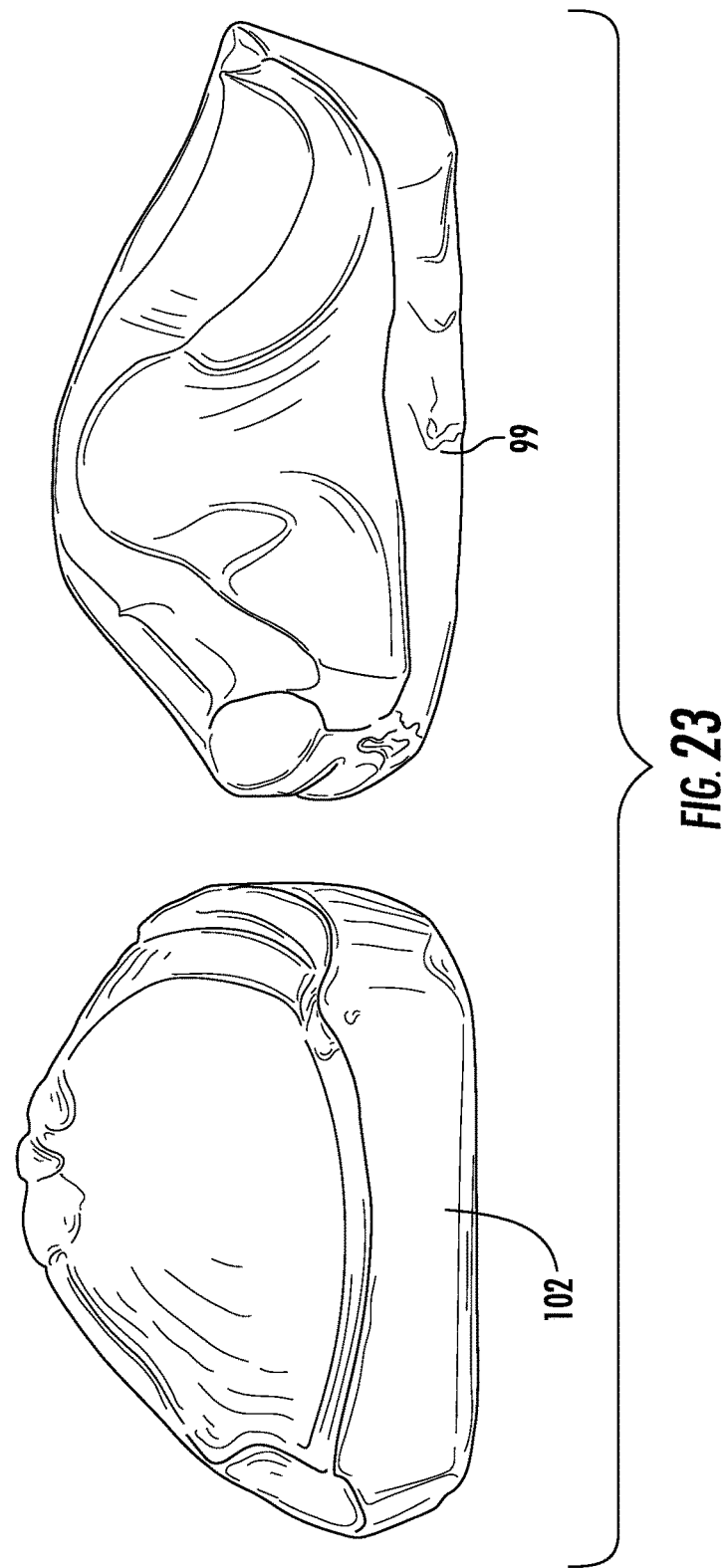
FIG. 23 is a rear and top perspective view of the stone models shown in FIG. 22.

FIG. 22 shows the positive stone model impressions formed by the use of the impressions first formed by the negative impressions formed by the upper and lower trays. These are made from conventional dental stone and molding trays. They are used to form the custom trays 90 and 92. Dental stone models 99 and 102 correspond to the positives produced from the negative impressions. These dental stone molds correspond to the structure, shape, size and individuality of the patient's mouth. FIG. 23 shows the same dental stone forms 99 and 102 as shown in FIG. 22, but from the rear of the items.

To use the upper and lower trays 61 and 30, in the mouth of a patient, a first main frame 20 is provided, as seen in FIGS. 1-3, which is adapted to releasably secure to the two trays, one for the upper portion of the mouth and one for the lower anatomy of the mouth. First main frame 20 is preferably metallic and provided with a plurality of telescopic columns 22 which protrude through and out each end of the first main frame. The columns, preferably three, are provided with magnetic connectors on each end thereof, 24a and 24b, which are adapted to connect to opposing small magnetic holding areas 33 or sockets on the platforms 32 of the upper and lower trays. The columns 22 are telescopic tubes and are provided, preferably in the middle of the height of the columns (at the point at which they are captured within first main frame 20), with spherical surfaces 23 or ball pivots (which are held within socket-like holding places in the main frame 20). The spherical surfaces 23 provide the columns with six degrees of freedom for desired placement and angle of the trays to be connected thereto in relation to the patient's anatomy and the main frame 20. First main frame 20 is also provided with at least one locking mechanism 26. Preferably, locking or set screw 26 (coupled to the various mechanical pieces and sliding surfaces within middle layer 105 of the main frame 20) is adapted to be tightened by means of a Allen wrench which acts on the head of the set screw 26, which will push the pressure plate, the side plate, the rear plate and the front plate, within the confines of the inside wall 210 of the middle layer 105, to squeeze around the spherical surfaces 23 of the telescopic columns 22 to secure the columns in a desired location, orientation, and height.

FIGS. 4 and 5 disclose first main frame 20 removably connected to a lower tray 30 and to an upper palatal tray 40 by means of the metallic connectors 24a and 24b, respectively. Lower tray 30 is preferably shaped to fit the curvature of the lower gums, generically, so that when filled with dental impression material it can be placed down onto the gum-line of a person who is edentulous and the impression material will mold and cure to its exact configuration. Lower tray 30 will be provided with impression material which is preferably made of a flexible, formable material, capable of being shaped in the exact configuration of the gum line. Once in place, lower tray 30 can be placed (using the convenient handle) down onto the gums, and the impression material will mold into the exact curvature and formation of the lower gum line, and will cure and harden in that configuration. An upper tray can be used which is quite similar to that of the lower tray for taking the impression of the upper gums and roof of the mouth of the patient. The upper tray, too, will generally match the upper gum line and roof. It, too, will be first filled with soft impression material, then lifted into the patient's mouth and placed along the upper gums and the roof of the mouth, and, as the impression material molds and cures, provides an accurate mold of the upper region of the mouth. Upper and partial palatal tray 40 is designed to replace the upper impression formed by the upper tray 61 for use of the main frame (I or II, elements 20 or 50, respectively) as it is believed that use of a full lower tray, an impression therein, the main frame and a full upper tray with impression may just be too much for a patient to comfortably hold in position during the subsequent steps. Thus, palatal tray 40 has been provided to allow the main frame, with the lower tray and the palatal tray, to serve as the dental articulator. According to the preferred embodiment of the present invention, the palatal tray 40 substitutes for the full upper tray 61 but, of course, the upper tray with impression material therein can be used. According to the preferred embodiment of the present invention, the upper tray 61 and the formed impression of the upper gums and the roof of the mouth is placed aside until needed for use, later (in creating a stone mold of the upper).

Lower tray 30 and a matching upper tray 61 may be too bulky on first main frame 20 to fit comfortably in the mouth of a user. Accordingly, when lower tray 30 is secured to first main frame 20 by means of magnetic connectors 24a, an upper palatal tray 40 can be substituted and placed over and secured to the top of first main frame 20 by means of magnetic connectors 24b and magnetic holding areas 33 on platforms 32 of upper palatal tray 40. Palatal tray 40 is designed to fit within the general curvature of the roof of a patient's mouth and provide a dentist with the correct height of the mouth for creation of dentures. Upper palatal tray 40 will, with the main frame and the telescopic columns or screws, be capable of moving in all directions necessary to match the anatomy, size, and curvature of the mouth, when a patient closes his mouth naturally around the main frame with palatal tray and lower tray therein. This forces the telescopic columns 22 (or telescopic screws 52) into an orientation (height, tilt, shift, etc.) which matches the mouth, and is able to do so by means of the six degrees of freedom provided to columns 22 (by spherical surfaces 23; by telescopic screws 52 of main frame II, element 50). Once upper palatal tray 40 is desirably properly located, with the lower tray 30 and cured dental impression of the lower gums in place, on the tray, with the main frame I or II, therebetween, with the dentist checking for proper bite, etc., the locking mechanism 26 can be turned, locking the columns 22 in place or the knurled nuts are screwed down to lock the telescopic screws in place, too. This is subsequent to the adjustments provided by the raising and lowering of the upper and lower portions of the telescopic screws, so that the palatal tray is against the roof of the patient, the lower tray with its impression, properly located, too. The use of the occlusal plane 70 is also helpful to determine proper positioning before the columns are secured in place and/or the telescopic screws locked into position.

As more fully described above, the lower tray 30 is preferably provided with a snap on and off, removably coupled handle 34, capable of attaching to the lower tray for controlling and directing the tray into the desired location in the mouth. The handle allows a dentist to properly position the tray(s) into the mouth along the upper and lower gums and hold them in place so that the impression material can harden.

In one embodiment, first main frame 20 can be used in combination with second main frame 50 or, main frame 50 can be used separately. Main frame 20 can be modified with a horizontal slit, means for securing sets of teeth, an occlusal plane, etc. Or, main frame II, element 50 can be used, by itself. If the two frames are to be used, the angle and dimensional interrelationship between the two needs to be "copied" from one main frame to the other so that whichever is used on and with the lower tray and its magnetic platforms and the palatal tray and its magnetic platforms, the same geometry of the patient's mouth is preserved.

In the other and preferred embodiment, first main frame 20 is not required to complete preparation of a set of dentures, and second main frame 50 can be used alone for all steps in the process. The preferred embodiment of the present invention comprises use solely of second main frame 50. However first or main frame I (element 20) has the advantage of providing more degrees of freedom of movement of the columns and shifting and tilting of the same with respect to the palatal and lower tray and the patient's anatomy so that it may be required in some dental procedures and not, for others.

Figure 7:
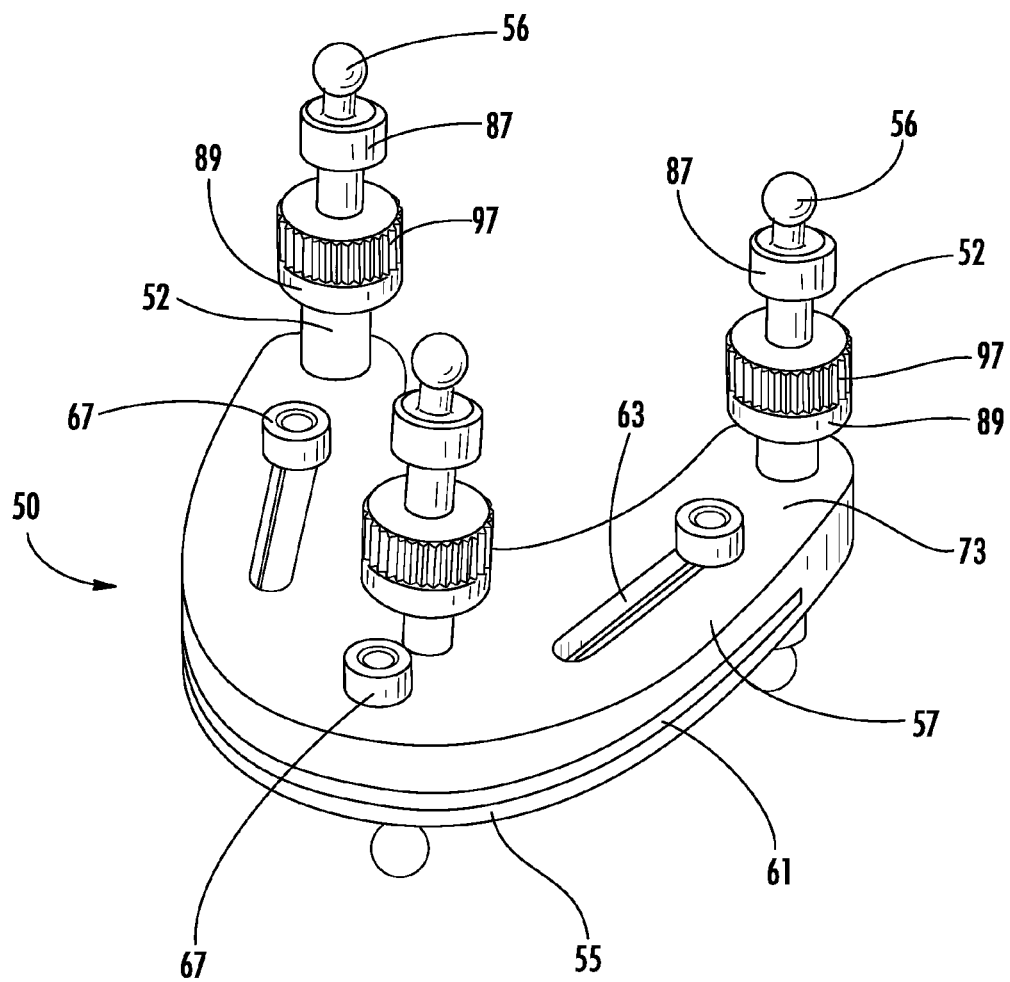
FIG. 7 is a front perspective view of the second main frame shown in FIG. 6.
Figure 8:
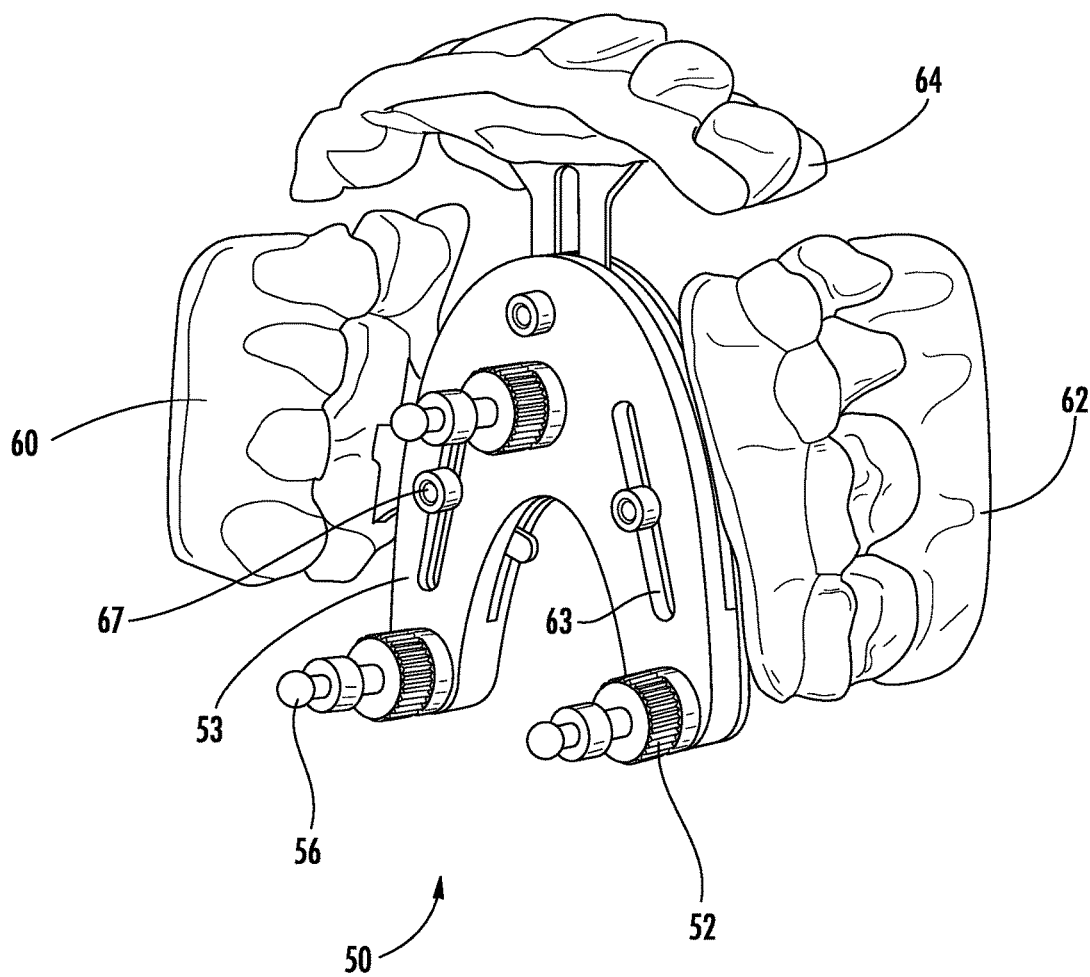
FIG. 8 is a top, rear perspective view of the second main frame shown in FIGS. 6 and 7, with sets or units of front, side and opposite side acrylic teeth, each in a substrate of wax, forming gums, attached thereto by rearwardly extending fork-like connectors which slide into and can be locked into a slit of the main frame.
Figure 9:
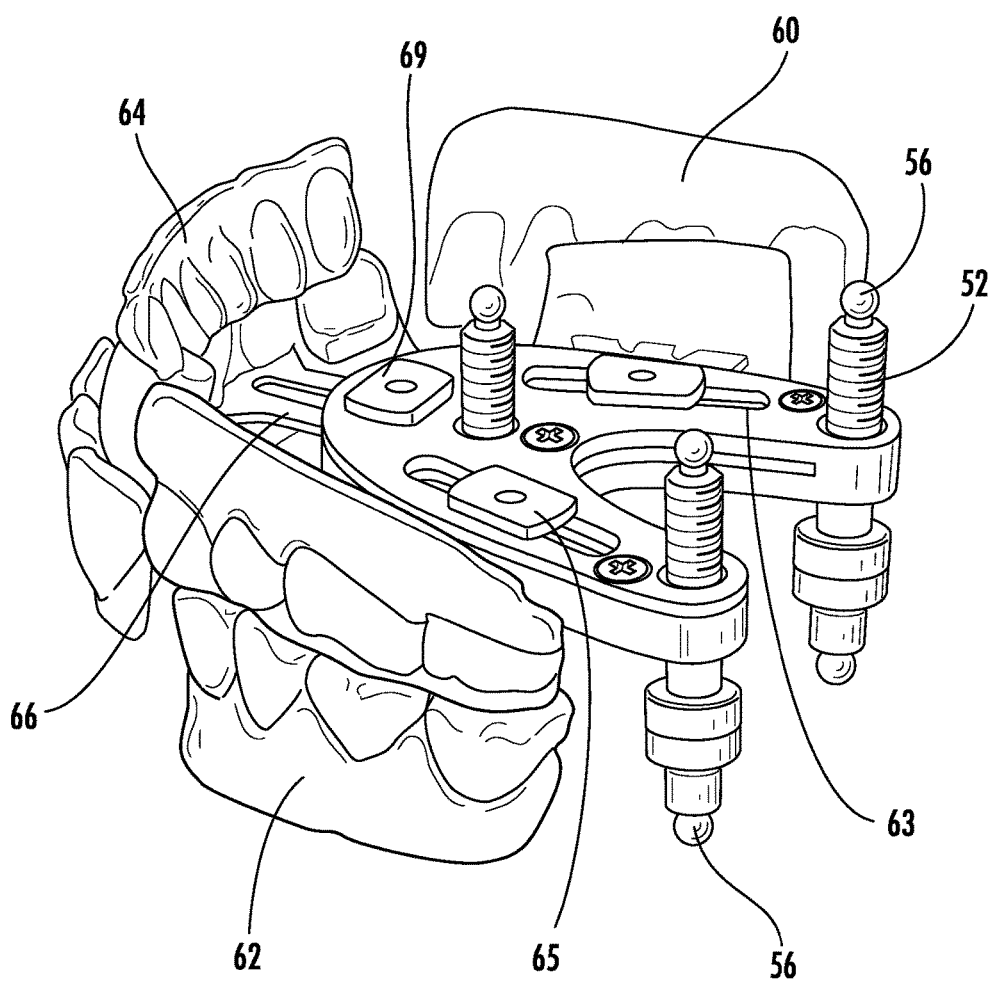
FIG. 9 is a rear, bottom or inverted (for illustration purposes) side perspective view of the second main frame shown in FIGS. 6, 7 and 8, with sets of teeth or units connected thereto and showing that the connecting forks surround a laterally slidable connector which can be locked in place.
Figure 10:
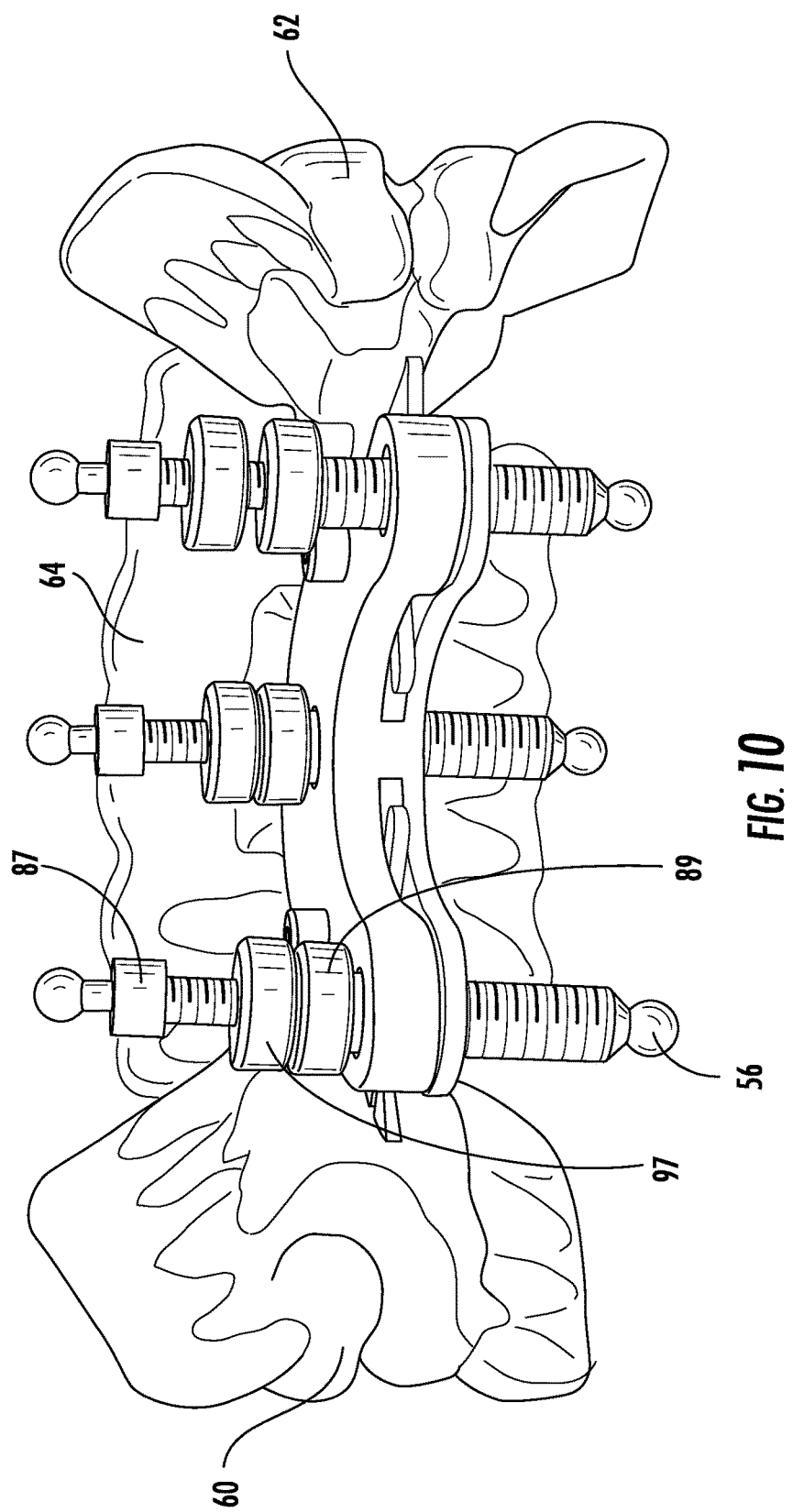
FIG. 10 is a rear perspective view of the second main frame shown in FIGS. 6, 7, 8 and 9, with sets or units of teeth connected thereto.
Figure 16A:
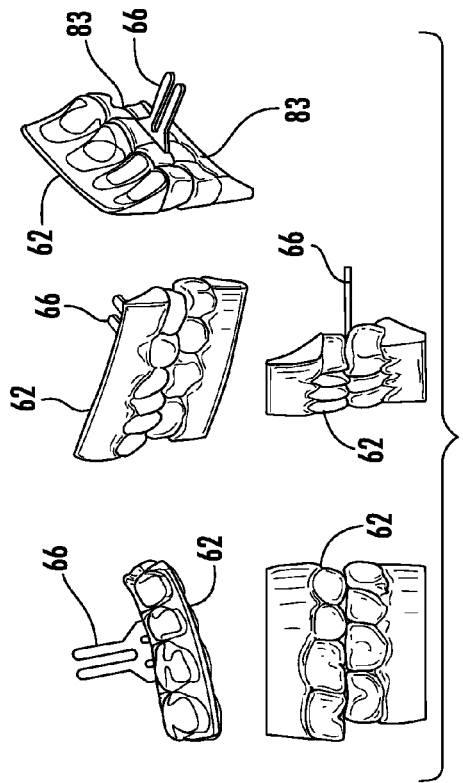
FIG. 16a shows various views (top, perspective, rear perspective, front, and side) of a set of front teeth or a "unit" to be used with the present invention, the unit having a fork-like connector extending rearwardly for placement into the horizontal slit of the main frame.
Figure 16C:
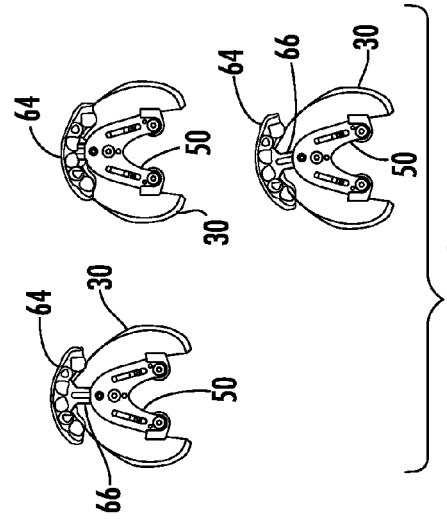
FIG. 16c shows various views (top, front perspective, rear perspective, front, and side) of a set of side teeth or another unit, to be used with the present invention, the teeth having a rearwardly projecting fork-like connector clip securable within the horizontal slit of the main frame.
Figure 16B:
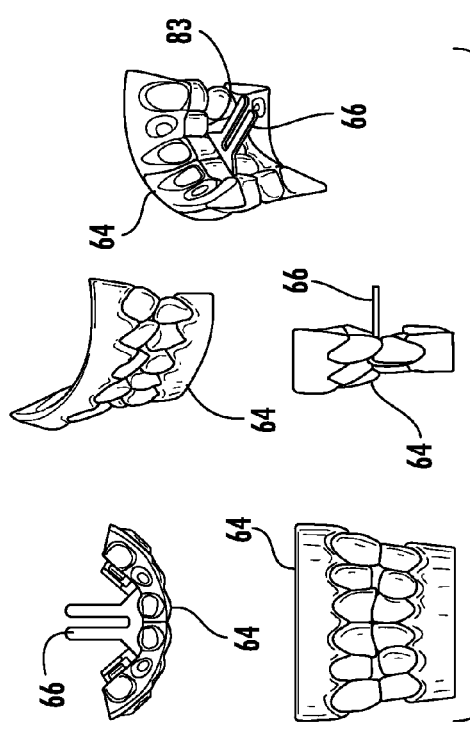
FIG. 16b shows various views (top, front perspective and front) of the front unit, secured to the main frame held by lower impression tray by a connector slid within the horizontal slit of the main frame.
Figure 16D:
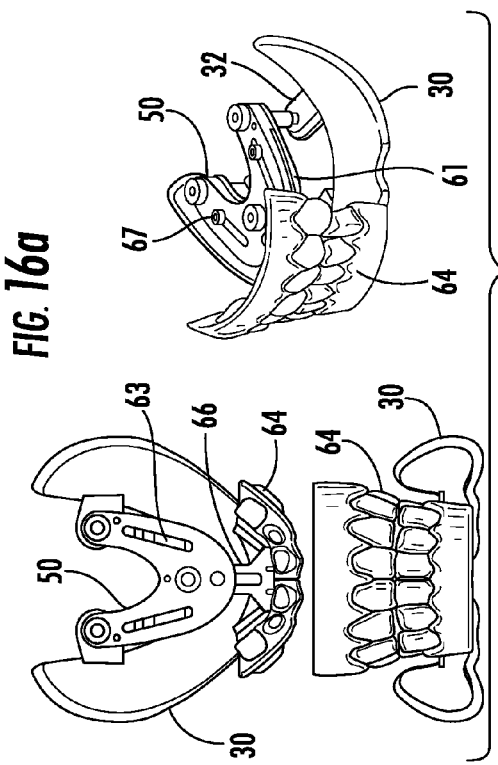
FIG. 16d shows three top perspective views of the front unit or set of front teeth as connected to the main frame (fork is held within the horizontal slit) and showing various positions of the front unit for proper alignment in the mouth of a user.

Second or main frame II, element 50, shown in FIGS. 6 and 7, like first main frame 20, is preferably metallic and provided with a plurality of telescopic columns or telescopic screws 52. Each telescopic screw 52 is provided with magnetic nubs or ends 56 which are adapted to magnetically connect to button-like magnetic elements 31 of the platforms 32 of the lower tray 30 and palatal tray 40. Each telescopic screw 52 is preferably provided with two locking nuts 54 and 56. Locking nut 56 is used to move upper end 29 vertically within the telescopic screw or column 52 for desired height placement of the palatal tray, while locking nut 54 can be loosened to rotate the lower segment of the screws 56 to move the entire telescopic screws or column 52 vertically and then tightened to hold it in desired location. Main frame II (element 50) is provided with a slit 61 across its horizontal axis, in which various connector pieces (the fork 72 of the occlusal plane 70 and the forks 66 of the front teeth set 64, of the left side teeth 60 and the right side teeth 62) can be slid in and then secured thereto).

FIGS. 11a-f show various perspective and elevational views of releasable handle 34 when secured to lower tray 30. Lower tray 30 (like a matching upper tray) is provided with three platforms 32, each with a magnetic holding area 33 and each of those provided with a button-like magnetic element 31. These are adapted to attract and hold, until manually displaced by the dentist, the magnetic or ferromagnetic ends or nubs 24 or balls 56 of columns 22 (or telescopic screws 52) of first main frame 20 or main frame II of element 50. FIG. 11g shows the lower tray 30 as it would be placed into the mouth of a user by means of releasable handle 34 for proper placement therein. The designs of main frame I, element 20, second or main frame II (element 50), lower tray 30, and upper or palatal tray 40 are all novel and created for individual use and as a set of components to use with one another and according to the present invention—using the patient's actual mouth as the articulator in connection with creation of dentures.

FIG. 12a is a side elevational view of main frame I, element 20, attached by means of magnetic nubs or ends of the columns 22 to the platforms 32 of lower tray 30 and upper palatal tray 40. FIG. 12b shows compressible (spring biased outwardly towards length-wise extension) columns 22 with magnetic ends 24a and 24b. FIG. 12c shows the make-up of the columns 22 and having magnetic ends 24a and 24b and ball pivot 23 which, when held within the middle layer 105, provides the six degrees of freedom for movement of the columns 22. FIG. 12d provides the inner mechanical components of main frame II, element 20, and specifically the locking mechanism. When the front set screw 29 is tightened, the load is distributed to the three ball joints, creating radial pressure thereon and preventing the ball joints from further pivoting. Tightening the front set screw 21a will put pressure on the front pressure plate 27 which abuts front ball joint 23a. On the other side of the first ball joint 23a are two distributor plates which distribute load from front ball joint to the other two ball joints. Locking mechanism 26 can be turned, thereby separating the distributor plates 25 and putting simultaneous pressure on all three ball joints. Next to the distributor plates are rear pressure plates and a rear set screw. All pieces fit together in a configuration so as to provide free movement of the ball pivots prior to tightening. Once the locking mechanism 26 is turned, pressure is put on all three ball pivots, preventing further movement. FIG. 12e is a perspective exploded view of all components of first main frame 20.

FIGS. 12f-l show various views of main frame I, element 20, with lower tray 30 and palatal tray 40 in different relative positions based on the anatomy of the patient and the available six degrees of freedom of ball pivots of columns 22. FIG. 13a is a top perspective view of main frame I, element 20, with lower tray 30 and palatal tray 40, with the removable handle 34 secured to lower tray 30. FIG. 13b shows main frame I, element 20, with lower tray 30 and palatal tray 40 as it would be placed into the mouth of a patient by means of the removable handle 34.

FIGS. 14a-d show alternate views of main frame II, element 50, securely yet detachably connected to lower tray 30 and palatal tray 40. As can be seen, telescopic-elongating screws 52 include knurled knobs for facilitating the dentist's adjustment upwardly and downwardly of the upper portion of the rods and also for the upward and downward adjustment of the lower portion of the rods of the telescopic screws. One rod is screw threaded within the other and the outside rod of the telescopic screws is screw threaded into and through internal screw threads of the main frame 50. Thus, the location of the location nubs or balls 56 vis a vis the platforms 32 of both the lower tray 30 and the palatal tray 40 can be easily accomplished. Of course, the adjustment is facilitated by the use of the occlusal plane 70 and all is accomplished according to the anatomy of the patient's mouth and standard and conventional dental principles. A locking nut can be provided for securing the positioning (lengths) of the telescopic screws. When the proper distancing is established by the dentist, by turning the respective knurled knobs, then, the locking nut is tightened to hold the knurled knob in place so it cannot easily continue to accidentally rotate. These telescopic screws (best seen in FIG. 14e) comprise a small upper rod which is screw threaded into the lower rod of slightly greater diameter, with the latter having external screw threads for moving the same up and down within the legs 51 and 53 and the central arch, as they are provided with threaded bores. The knurled knobs 87, for the upper rod and 89 for the lower rod, facilitate turning and adjusting. The locking nut 91 is shown, too, in FIG. 14e. The telescopic screws 52 and knurled knobs 87, 89 and locking nut 91, can be seen in FIG. 14e, and it also shows the telescopic screws at minimum distance between the magnetic or ferromagnetic balls 56 and the maximum extended distance which can be achieved between the magnetic or ferromagnetic balls 56. These balls 56 are retained (until manually dislodged) on the button like magnetic elements 31 of platforms 32 of the lower tray 30 and the palatal tray 40, as shown in FIGS. 14b, 14c, 14d. The adjustability of the components, in height, tilt, both in forward and back orientation and side to side tilt, all by adjusting the telescopic screws are shown in FIGS. 14f through 14j.

FIG. 15a shows main frame II, element 50, also magnetically connected to lower tray 30. For ease of illustration, the palatal tray is not shown. To ensure proper orientation of the horizontal slit (and the teeth units to be attached thereto) in comparison to the anatomy of the patient, the occlusal plane is used. It has a rearwardly extending fork 72, which is slid into the horizontal slit 61 (see FIGS. 15*a* and 15*d*). The occlusal plane 70 is used to ensure the correct height, tilt, and orientation of dentures to be created by means of the present invention. The occlusal plane is positioned, once the second main frame 50 is placed into the mouth of a user along with the palatal tray, to provide an easily visible means to align the horizontal slit 61 of the main frame II, element 50, so that the same is parallel to the eyes, nose, and ala tragus of the patient, ensuring that the main frame II, element 50, has been placed in the proper alignment (by adjusting the telescopic screws 52) so that the dentures will not be crooked. This is all done consistent with standard dental principles. Then, using the locking nuts 97 on the telescopic screws 52 of the main frame 50, the final adjustment is ensured and then the locking nut turned to rest upon the knurled knob 89, to prevent further unintended movement of the same. The use of the occlusal plane 70 and the adjustment of the telescopic screws to the desired horizontal position of the horizontal slit can be seen in FIGS. 15*b* and 15*c* and resulting in FIG. 15*d*. As can be seen in FIG. 15*d*, the desired placement and height of the main frame and its horizontal slit 61, being attached to the palatal tray and the lower tray will result in the occlusal plane 70 being parallel with the ears, eyes, and ala tragus.

Once adjustment is made and the main frame locked into position, the dentist will start to assemble the units of teeth and attach the same to the main frame. A complete set of dentures is preferably made using three sets of teeth which are preferably made of acrylic. These teeth, in color, shape, size, etc. are the actual teeth which will be provided in the end product, a complete set of dentures. These individual acrylic teeth are currently available. However, the present invention sets the same into two waxed forms and, further, provides the same with rearwardly extending forks, the flanges of the forks being secured within the rear of the sets of teeth or units and the forks being sufficiently thin to slide into the horizontal slit 61 of the main frame II, element 50. These sets of teeth 60, 62, and 64 (two side sets and one anterior set) are provided to the dentist for selection, all with rearwardly projecting forks 66, comprised of a pair of parallel tines (fitting around the holding screws 67) within the horizontal slit 61 and flanges holding and securing the metallic fork to the waxed gums and acrylic teeth. The dentist can insert the teeth sets 60, 62 and 64 either before placement of the main frame II, element 50, into the patient's mouth or while the main frame II, element 50, lower tray 30 and palatal tray 40 is in the patient's mouth. The teeth can be dipped or run under warm water, if required, and this will soften one of the waxes of the sets of teeth to allow the dentist to slightly mold the curvature of the teeth to the arch, the sides—the actual anatomy of the patient. Each of the sets of teeth 60, 62, and 64 are provided with the fork 66 and those forks slide into the horizontal slit 61 and have tines on each side of the holding screws 67. The side teeth sets 62 and 60 can be arcingly adjusted forwardly and rearwardly by the sliding movement of the holding screws 67 and the plates 65 within the slots 63. Quickly and easily, the teeth are placed and adjusted in place onto the main frame II, element 50. This will provide a complete set of teeth with proper spacing, angling, and positioning for final creation of the dentures, since the use of the patient's own mouth as the articulator helps eliminate errors in the positioning and curvature of the dentures. Once the teeth are in place, the holding screws 67 are tightened by use of an L-shape Allen wrench or tool, as the heads of the holding screws are preferably Allen-wrench compatible. Now, a complete set of teeth (see FIG. 17*e*) are provided which can be formed, outside of the patient's mouth, into a set of dentures, using the impressions first formed by the upper tray 61 and the lower tray 30. However, it is important to note that the set of teeth, at this point in the procedure, are still attached to the main frame. Because the occlusal plane 70 has been used and because the teeth sets, 60, 62 and 64 are pre-formed in wax with both upper and lower associated teeth, because of the adjustment capability of the teeth within the confines of the horizontal slit 61, the teeth are perfectly aligned when locked into the main frame. This is shown (without the main frame for ease of illustration) in FIGS. 17*c* and 17*e*.

Element 300 in figures 17*d* and 17*e* shows the rear surface of two of the side set of teeth 62 and 60, respectively.

Now the dentures are to be formed, comprising the actual teeth of the sets of teeth 60, 62 and 64 as installed into the main frame II, element 50, with artificial or acrylic gums and a roof segment, also formed of acrylic. In this connection, the conventionally available articulator 80 is used (see FIGS. 18 and 19). Once removed from the mouth, the lower tray 30 can be removed from the second main frame 50. The upper and lower custom trays 90 and 92 (see FIGS. 20 and 21) are formed from the stone models of the negative impressions first formed from the upper tray 61 and the lower tray 30. Stated differently, the negative impressions first formed by the dentist are used for forming stone positives, see FIGS. 22 and 23. Those, then, are used to form custom trays, as seen in FIGS. 20 and 21. Conventionally available impression trays are available and can be used for pouring of the positives of the impressions from dental stone. These positives, 99 and 102 are shown in FIGS. 22 and 23. The dental stone fills in the gaps of the impressions, thereby creating a positive impression of the patient's mouth, the lower gums and the upper gums and including the roof, as it will form around the negative impression made by the impressions of the patient's mouth, from a complete upper tray 61 and lower tray 30. The stone models will correspond precisely to the patient's mouth, with one stone model 102 matching the curvature and shape of the upper mouth, gums and roof and one stone model 99 matching that of the lower gums of the patient's mouth. These stone models can be seen in FIGS. 22 and 23.

After the stone models are complete, the custom trays or impressions 90 and 92 are made from the stone models 99 and 102, respectively. Light-curable sheets of wax-like material can be placed over the upper and lower stone models 99 and 102 and manually pushed and maneuvered into place along the positive impression portions of the stone models to form a thin, wax, custom negative impression tray of the top and bottom of the patient's mouth. These are the custom trays of FIGS. 20 and 21. Then, after pressing the sheets into the curves and crevices, and forms of the stone models, the sheets are cured to preserve their shape and form custom trays 90 and 92. When cured with light, the custom trays 90 and 92 will set in place and form negatives of the patient's mouth (just as the original impression material did when the upper tray 61 and the lower tray 30 were used). These will fit perfectly onto the positives of the stone models.

A standard dental articulator can be used as a holding unit for the stone models, the custom trays, and the main frame and palatal and lower tray. This standard articulator 80 can be seen in FIG. 18. Quick setting and first soft dental plaster 110 can be placed on the flat bottom and top surfaces, respectively, of the lower and upper stone models and then they are placed onto the flat surface of the top plane and the flat surface of the bottom plane of the articulator 80. The lower stone model 99, with the lower tray 30 in place thereon, and with the custom tray are thus placed onto the mechanical articulator 80. This will be held in place by the quick setting dental plaster 110. Similarly, the upper stone model 102 and the palatal tray 40, with the upper custom tray are located in the mechanical articulator 80. The quick setting dental plaster 110 will solidify.

The mechanical articulator thus holds a "dental sandwich" starting from the top to the bottom, as follows: the underneath portion of the top surface of the conventional articulator 80; originally soft but soon-to-harden dental plaster 110; secured thereto will be the flat surface of the upper stone model 102, with the positive of the stone model in the position as if replicating the patient's mouth; i.e., the set of stone gums and roof, will be provided with the custom tray 92 of the roof of the mouth and the upper gums; then below it will be the palatal tray 40; which is supported on the main frame II, element 50; the main frame with secured teeth units, which is supported on lower tray 30; which contains the custom tray 90 of the lower gums; which then sits upon the positive of the gums of the lower mouth, formed on the stone model 99, (flat side of the stone model 99 being faced down); which then has quick-to-harden dental plaster 110; sitting directly upon the bottom flat surface of the conventional articulator 80. Quick setting dental plaster 110 is used and poured on top of the upper stone model and beneath the lower stone model to fill in the gap between the top of the upper stone model 102 and the articulator 80, and the bottom of the lower stone model 99 and the articulator, thereby holding all pieces—stone models, custom trays, main frame II, element 50, palatal and lower trays—in place at a desired orientation for the patient's mouth. Dental plaster 110 is used and poured below the lower stone model 99 to fill in the gap between the bottom (flat) of the lower stone model and the conventional articulator. This serves to hold all components in place in the conventional articulator 80 with the main frame 50, and teeth 60, 62, and 64, and the custom trays, contained therein. If the configuration of the stone models, the upper and lower trays—each with custom trays, are done accurately, along with adjustment of the main frame vis a vis the anatomy of the patient's mouth, by use of the telescopic screws 52, a substantially perfect reconstruction of the mouth has been made and is set forth in the conventional articulator with the acrylic teeth shown as they will be displayed in a final set of dentures.

The custom trays 90 and 92 are substituted for the negative impressions first formed in the lower tray 30 and above the palatal tray 40. The impressions can be discarded as they were primarily used for the making of the stone models and for fitting of the trays and the main frame into the patient's mouth.

FIG. 19 shows the "dental sandwich" with the stone models 99 and 102 placed between the top and bottom surfaces of the articulator 80, and with dental plaster 110 used to fill in the gap between the plates of the articulator 80 and the flat surfaces of the stone models. However, this image is seen prior to baseplate wax being formed to close the gaps between the custom trays 90 and 92 and the wax of the sets of teeth, 60, 62, and 64 (only a portion of set 64 is shown).

Once the custom trays 90 and 92 are secured to the stone models 99 and 102, respectively, by use of dental plaster 110, commercially available baseplate dental wax can be heated up and manually attached to close the gap between the custom trays and the tops of the waxed teeth for the uppers and the bottom of the waxed teeth for the lowers. The baseplate dental wax connects the custom trays 90 and 92 to the wax attached to the sets of teeth 60, 62, and 64 (already secured to the main frame II, element 50, by the forks 66) so as to leave no gaps between the custom trays and the wax of the teeth. This dental base-plate wax will become malleable once heated, and is adapted to be inserted along any ridges or troughs in the custom trays. The combination of baseplate wax and custom trays and the wax of the teeth will create a mold of the gums of the patient so as to perfectly match that patient's mouth, and connect the teeth sets to the custom trays. This will provide a dentist with the correct anatomy, height and depth of the dentures with teeth properly positioned. The custom trays are the wax equivalent of the acrylic of the dentures. This step can be performed for both the lower and upper custom trays. Once the baseplate wax is set, the forks 66 and wax substrate of the teeth, including that which holds the upper teeth to the lower teeth, can be removed by re-heating the teeth at a lower temperature than that which would melt the base-plate wax, thereby leaving a set of dentures matching the curvature and shape of the mouth with the teeth properly located and upper teeth separated from lower teeth. The lower temperature-melting wax will melt away, disengaging the upper teeth from the lower teeth and the forks from the teeth.

At this point, standard dental principles and procedures can be used to create the final set of dentures from the custom trays, the baseplate wax and the acrylic teeth. A set of upper and lower complete dentures will be formed with the teeth precisely positioned as they were in the main frame. The main frame can be reused for the next patient. The same acrylic teeth as used with the main frame II, element 50, can be used in the dentures provided to the patient and the dentures can be made with a perfectly molded set of "gums" which match the angle, curvature, and shape of the particular patient's mouth, so that the dentures will fit the mouth, with the teeth aligned and in place, all as desired.

The present invention presents a system, components and method for accurate creation of a set of dentures using the patient's mouth as the articulator, as well as a process which can be completed in a single visit.

It will be understood by those of ordinary skill in the art that various changes may be made and equivalents may be substituted for elements without departing from the scope of the invention. In addition, many modifications may be made to adapt a particular feature or material to the teachings of the invention without departing from the scope thereof. Therefore, it is intended that the invention not be limited to the particular embodiments disclosed, but that the invention will include all embodiments falling within the scope of the claims.

What is claimed:

1. A set of dental devices for use in creating artificial dentures using the patient's mouth as an intra-oral articulation mechanism comprising a) a palatal member shaped to the general shape of the palatal arch of the mouth of a patient b) a lower tray having an arcuate and inverted trough for use in creating a negative impression of the lower gums of the mouth of the patient, said lower tray comprising at least three inwardly directed and horizontally arranged, magnetic-attracting holding platforms and c) a mechanical frame which arcuately extends from a first side, across the front and then to the other side of the patient's mouth, said frame further comprising at least three vertically telescopic supports with magnetic ends, said supports being spaced apart as said holding platforms are spaced and a horizontal slit in said frame for accepting the adjustable placement of a rearward mechanical extension of a set of artificial teeth therein, said frame adapted to fit within the patient's mouth and said magnetic ends of said supports being magnetically supportable upon said holding platforms of said lower tray, said palatal member, lower tray and said frame having magnetic and mechanical connections for removably securing said palatal member to said frame and said lower tray to said frame and wherein said supports are adjustable in three dimensions, yet having a support locking mechanism holding the relative location of said magnetic ends of said supports with respect to said holding platforms of said lower tray and with respect to said palatal member.

2. A system as claimed in claim 1 further comprising a set of artificial teeth having rearward mechanical projections for selective securement into said horizontal slit of said frame.

3. A system for creating artificial teeth for a patient using the patient's mouth as an intra-oral articulator comprising:
 a lower dental tray for creating a dental impression of the lower gum ridge of the patient's mouth;
 an upper dental tray for creating a dental impression of at least a portion of the patient's upper mouth portion including the palatal arch; and
 an artificial-tooth holding device in contact with said lower dental tray and having selective adjustment about multiple degrees of movement and then fixed securement with respect to said lower dental tray while within the patient's mouth, said artificial tooth holding device further comprising a tooth holding, horizontal slit wherein one or more artificial teeth provided with a rearwardly projecting tine can slide into and are movable within said slit for initial adjustably holding and then securing artificial teeth thereon.

4. A system as claimed in claim 3 further comprising a set of one or more artificial teeth held in wax with rearwardly projecting tines projecting therefrom.

5. A system as claimed in claim 3 further comprising a thin-profile, arc-shaped, occlusal plane for selectively securement to and removal from said artificial tooth holding device.

6. A system as claimed in claim 5 wherein said occlusal plane is provided with a rearwardly extending projection for selective placement into the same or a second of said slit provided to said artificial tooth holding device.

7. A system as claimed in claim 3 wherein said artificial tooth holding device is magnetically secured to said upper and/or lower tray.

* * * * *